US006974572B2

(12) United States Patent
Morsey et al.

(10) Patent No.: US 6,974,572 B2
(45) Date of Patent: Dec. 13, 2005

(54) NON-ANAPHYLACTOGENIC IGE FUSION PROTEINS

(75) Inventors: Mohamad A. Morsey, Niantic, CT (US); Tracy M. Brown, Ashaway, RI (US)

(73) Assignees: Pfizer, Inc., New York, NY (US); Pfizer Products, Inc., Groton, CT (US)

( * ) Notice: Subject to any disclaimer, the term of this patent is extended or adjusted under 35 U.S.C. 154(b) by 153 days.

(21) Appl. No.: 10/152,190

(22) Filed: May 21, 2002

(65) Prior Publication Data

US 2003/0096369 A1 May 22, 2003

Related U.S. Application Data

(60) Provisional application No. 60/292,638, filed on May 22, 2001.

(51) Int. Cl.[7] ...................... A61K 39/395; A61K 39/00; C12P 21/08

(52) U.S. Cl. ............................... 424/133.1; 424/185.1; 424/192.1; 530/387.3

(58) Field of Search .......................... 424/133.1, 185.1, 424/192.1, 185; 530/387.3, 324

(56) References Cited

U.S. PATENT DOCUMENTS

| 5,601,821 A | | 2/1997 | Stanworth et al. | |
|---|---|---|---|---|
| 5,629,415 A | * | 5/1997 | Hollis et al. | 536/23.53 |
| 5,653,980 A | * | 8/1997 | Hellman | 424/184.1 |

FOREIGN PATENT DOCUMENTS

| EP | 0 263 655 | | 4/1988 |
|---|---|---|---|
| WO | WO 92/20316 | | 11/1992 |
| WO | WO 92/22635 | | 12/1992 |
| WO | WO 93/14188 | | 7/1993 |
| WO | WO 93/20221 | | 10/1993 |
| WO | WO 94/08598 | | 4/1994 |
| WO | WO 95/26365 | * | 10/1995 |
| WO | WO 97/31948 | | 9/1997 |

OTHER PUBLICATIONS

Stryer et al, in Biochemistry, Third edition, W H Freeman Company, New York, pp. 31–33, 1998.*
Ngo et al, 1994, The Protein Folding Problem and Tertiary Structure Prediction, pp. 492–495.*
Kuby et al., 1994, Immunology, second edition, pp. 85–96.*
Abaza et al, J of Protein Chemistry 11(5): 433–444, 1992.*
David S. Burt, et al., "Inhibition of Binding of Rat IgE to Rat Mast Cells by Synthetic IgE Peptides", *Eur. J. Immunol.*, vol. 17, pp. 437–440, (1987).
Birgit Helm, et al., "The Mast Cell Binding Site on Human Immunoglobulin E", *Nature*, vol. 331, pp. 180–183, (1988).
Birgit Helm, et al., "Blocking of Passive Sensitization of Human Mast Cells and Basophil Granulocytes with IgE Antibodies by a Recombinant Human ε–chain Fragment of 76 Amino Acids", *Proc. Natl. Acad. Sci.*, vol. 86, pp. 9465–9469, (1989).
Donata Vercelli, et al., "The B–Cell Binding Site on Human Immunoglobulin E", *Nature*, vol. 338, pp. 649–651, (1989).
Noriki Nio, et al., "Inhibition of Histamine Release by Synthetic Human IgE Peptide Fragments: Structure–Activity Studies", *Peptide Chemistry*, pp. 203–208, (1990).
Noriki Nio, et al., "Inhibition of Passive Sensitization of Human Peripheral Basophils by Synthetic Human Immunoglobulin E Peptide Fragments", *FEBS*, vol. 319, No. 3, pp. 225–228, (1993).
Noriki Nio, et al., "Inhibition of Passive Cutaneous Anaphylaxis by Synthetic Human Immunoglobulin E Peptide Fragments", *FEBS*, vol. 314, No. 3, pp. 229–231, (1992).
Mitali Basu, et al., "Purification and Characterization of Human Recombinant IgE–Fc Fragments that Bind to the Human High Affinity IgE Receptor", *The Journal of Biological Chemistry*, vol. 268, No. 18, pp. 13118–13127, (1993).
Luca Vangelista, et al., "The Immunoglobulin–Like Modules Cε3 and α2 are the Minimal Units Necessary for Human IgE–FcεRI Interaction", *The Journal of Clinical Investigation*, vol. 103, No. 11, pp. 1571–1578, (1999).
Michael W. Robertson, et al. "IgE Structure–Function Relationships Defined by Sequence Directed Antibodies Induced by Synthetic Peptides", *Molecular Immunology*, vol. 25, No. 2, pp. 103–113 (1988).
Shelley Schwarzbaum, et al., "Mapping of Murine IgE Epitopes Involved in IgE–Fcε Receptor Interactions", *Eur. J. Immunol.*, vol. 19, pp. 1015–1023, (1989).
Marla Weetall, et al., "Mapping the Site of Interaction Between Murine IgE and its High Affinity Recpetor with Chimeric Ig[1]", *The Journal of Immunology*, vol. 145, No. 11, pp. 3849–3854, (1990).
Leonard Presta, et al., "The Binding Site on Human Immunoglobulin E for its High Affinity Receptor", *The Journal of Immunology of Biological Chemistry*, vol. 269, No. 42, pp. 26368–26373, (1994).
Ahuva Nissim, et al., "Fine Specificity of the IgE Interaction with the Low and High Affinity Fc Receptor[1]", *The Journal of Immunology*, vol. 150, No. 4, pp. 1365–1374, (1993).

(Continued)

*Primary Examiner*—Christina Chan
*Assistant Examiner*—Phuong Huynh
(74) *Attorney, Agent, or Firm*—Scully, Scott, Murphy & Presser

(57) ABSTRACT

The present invention provides compositions and methods for the use of antigenic peptides derived from the Fc portion of the epsilon heavy chain of IgE molecules from two unrelated species as vaccines for the treatment and prevention of IgE-mediated allergic disorders. In particular, the invention provides compositions for the treatment and prevention of IgE-mediated allergic disorders comprising an immunogenic amount of one or more antigenic peptides.

3 Claims, 1 Drawing Sheet

OTHER PUBLICATIONS

Jaime Moscoso Del Prado, et al., "Monoclonal Antibodies Against Human IgE Identification of an Epitope Sharing Properties with the High–Affinity Receptor Binding Site", *Molecular Immunology*, vol. 28, No. 8, pp. 839–844, (1991).

Achsah DKeegan, et al., "Characterization of New Rat Anti–Mouse IgE Monoclonals and Their Use Along With Chimeric IgE to Further Define the Site that Interacts with FcεRII and FcεRI", *Molecular Immunology*, vol. 28, No. 10, pp. 1149–1154, (1991).

William A. Hook, et al., "Monoclonal Antibodies Defining Epitopes on Human Ige", *Molecular Immunology*, vol. 28, No. 6, pp. 631–639, (1991).

Hiroshi Takemoto, et al., "Anti–Human IgE Monoclonal Antibodies Recognizing Epitopes Related to the Binding Sites of High and Low Affinity IgE Receptors", *Microbiol. Immunol.*, vol. 38, No. 1, pp. 63–71, (1994).

Michal Baniyash, et al., "Anti–IgE Monoclonal Antibodies Directed at the Fcε Receptor Binding Site", *Molecular Immunology*, vol. 25, No. 8, pp. 705–711, (1988).

Tse Wen Chang, "The Pharmacological Basis of Anti–IgE Therapy", *Nature Biotechnology*, vol. 18, pp. 157–162, (2000).

Leonard G. Presta, et al., "Humanization of an Antibody Directed Against IgE", *The Journal of Immunology*, vol. 151, No. 5, pp. 2623–2632, (1993).

Beda M. Stadler, et al., "Biological Activites of Anti–IgE Antibodies", *Int Arch Allergy Immunol.*, vol. 102, pp. 121–126, (1993).

Michael P. Rudolf, et al., "Epitope–Specific Antibody Response to IgE by Mimotope Immunization", *The Journal of Immunology*, vol. 160, pp. 3315–3321, (1998).

Barry R. Goldspiel, et al., "Human Gene Therapy", *Clinical Pharmacy*, vol. 12, pp. 488–505, (1993).

George Y. Wu, et al., "Delivery Systems for Gene Therapy", *Biotherapy*, vol. 3, pp. 87–95, (1991).

Paul Tolstoshev, "Gene Therapy, Concepts, Current Trials and Future Directions", *Annu. Rev. Pharmacol. Toxicol.*, vol. 32, pp. 573–596, (1993).

Richard C. Mulligan, "The Basic Science of Gene Therapy", *Science*, vol. 260, pp. 926–932, (1993).

Richard A. Morgan, et al., "Human Gene Therapy", *Annu. Rev. Biochem.*, vol. 62, pp. 191–217, (1993).

Beverly H. Koller, et al., "Inactivating the $\beta_2$–Microglobulin Locus in Mouse Embryonic Stem Cells by Homologous Recombination", *Proc. Natl. Acad. Sci.*, vol. 86, pp. 8932–8935 (1989).

Maarten Zijlstra, et al., "Germ–line Transmission of a Disrupted $\beta_2$–Microglobulin Gene Produced by Homologous Recombination in Embryonic Stem Cells", *Nature*, vol. 342, pp. 435–438, (1989).

George Y. Wu, et al., "Receptor–Mediated in Vitro Gene Transformation by a Soluble DNA Carrier System", *The Journal of Biological Chemistry*, vol. 262, No. 10, pp. 4429–4432, (1987).

A. Dusty Miller, et al., "Use of Retroviral for Gene Transfer and Expression", *Methods in Enzymology*, vol. 217, No. 76, pp. 581–599, (1990).

Monika M. Clowes, et al., "Long–Term Biological Response of Injured Rat Carotide Artery Seeded with Smooth Muscle Cells Expressing Retrovirally Introduced Human Genes", *J. Clin. Invest.*, vol. 93, pp. 644–651, (1994).

Karen F. Kozarsky, et al., "Gene Therapy: Adenovirus Vectors", *Current Opinion in Genetics and Development*, vol. 3, pp. 499–503, (1993).

Christopher E. Walsh, et al., "Gene Therapy for Human Hemoglobinopathies", *P.S.E.B.M.*, vol. 204, pp. 289–300, (1993).

Jean–Philippe Loeffler, et al., "Gene Transfer in Primary and Established Mammalian Cell Lines with Lipopolyamine–Coated DNA", *Methods in Enzymology*, vol. 217, pp. 599–619, (1993).

Derek L. Stemple, et al., "Isolation of a Stem Cell for Neurons and Glia from the Mammalian Neural Crest", *Cell*, vol. 71, pp. 973–985, (1992).

James G. Rheinwald, "Serial Cultivation of Normal Human Epidermal Keratinocytes", *Methods in Cell Biology*, vol. 21A, pp. 229–254, (1980).

Mark R. Pittelkow, M.D., et al., "New Techniques for the In Vitro Culture of Human Skin Keratinocytes and Perspectives on their Use for Grafting of Patients with Extensive Burns", *Mayo Clinic Proceedings*, vol. 61, pp. 771–777, (1986).

Robert Langer, "New Methods of Drug Delivery", *Science*, vol. 249, pp. 1527–1533, (1990).

* cited by examiner

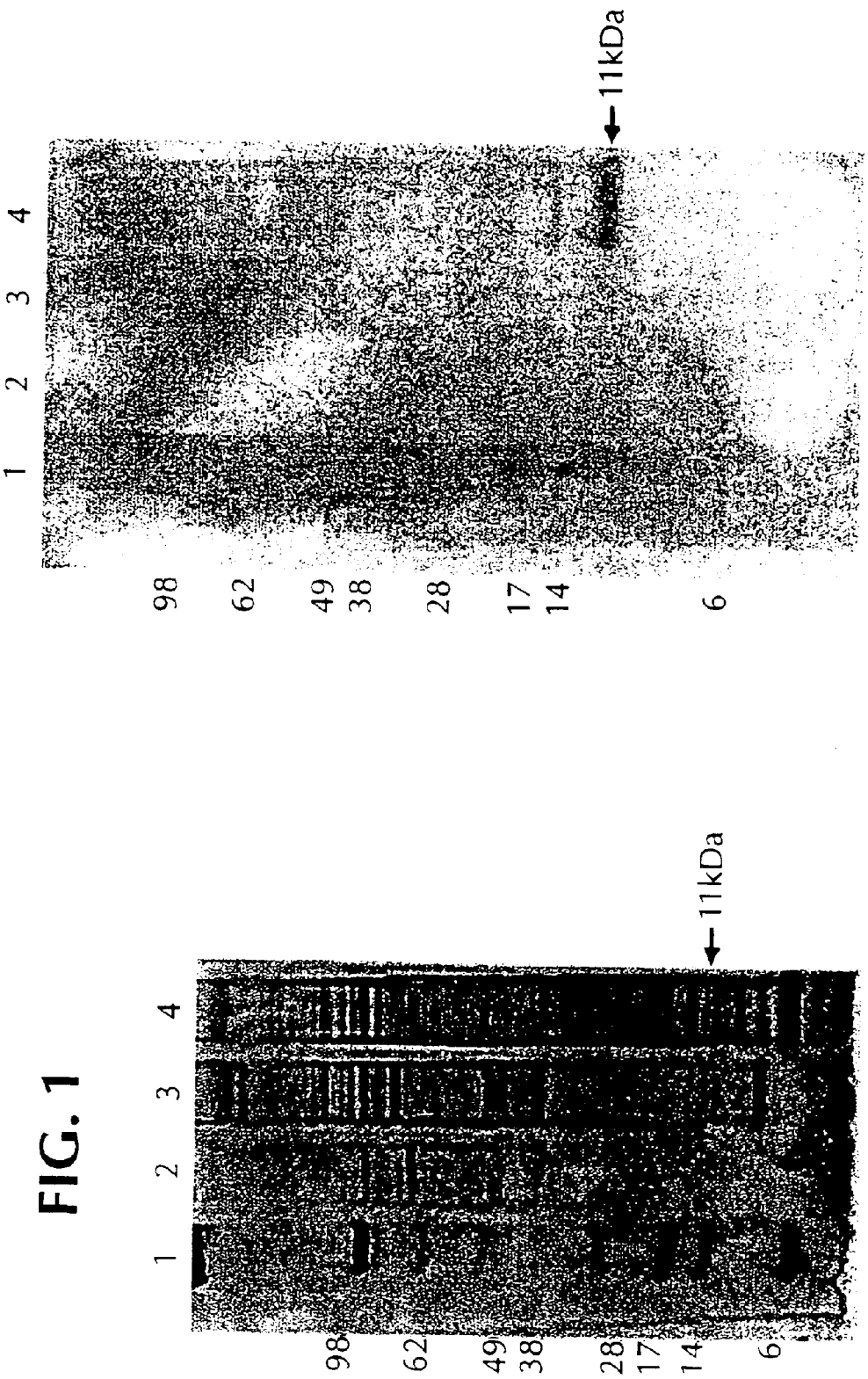

SEQUENCE LISTING

<160> NUMBER OF SEQ ID NOS: 28

<210> SEQ ID NO 1
<211> LENGTH: 114
<212> TYPE: PRT
<213> ORGANISM: Dog CH3 domain

<400> SEQUENCE: 1

Ser Glu Ser Asp Pro Arg Gly Val Thr Ser Tyr Leu Ser Pro Pro Ser
 1               5                  10                  15

Pro Leu Asp Leu Tyr Val His Lys Ala Pro Lys Ile Thr Cys Leu Val
            20                  25                  30

```
Val Asp Leu Ala Thr Met Glu Gly Met Asn Leu Thr Trp Tyr Arg Glu
            35                  40                  45

Ser Lys Glu Pro Val Asn Pro Gly Pro Leu Asn Lys Lys Asp His Phe
 50                  55                  60

Asn Gly Thr Ile Thr Val Thr Ser Thr Leu Pro Val Asn Thr Asn Asp
 65                  70                  75                  80

Trp Ile Glu Gly Glu Thr Tyr Tyr Cys Arg Val Thr His Pro His Leu
                85                  90                  95

Pro Lys Asp Ile Val Arg Ser Ile Ala Lys Ala Pro Gly Lys Arg Ala
            100                 105                 110

Pro Pro

<210> SEQ ID NO 2
<211> LENGTH: 117
<212> TYPE: PRT
<213> ORGANISM: Human CH3/dog CH3 domain fusion

<400> SEQUENCE: 2

Cys Ala Asp Ser Asn Pro Arg Gly Val Ser Ala Tyr Leu Ser Arg Pro
 1               5                  10                  15

Ser Pro Phe Asp Leu Phe Ile Arg Lys Ser Pro Thr Ile Leu Cys Leu
            20                  25                  30

Val Leu Asp Leu Ala Pro Ser Lys Gly Thr Val Gln Leu Thr Trp Ser
            35                  40                  45

Arg Ala Ser Gly Lys Pro Val Asn His Ser Thr Arg Lys Glu Glu Lys
 50                  55                  60

Asp His Phe Asn Gly Thr Ile Thr Val Thr Ser Thr Leu Pro Val Asn
 65                  70                  75                  80

Thr Asn Asp Trp Ile Glu Gly Glu Thr Tyr Tyr Cys Arg Val Thr His
                85                  90                  95

Pro His Leu Pro Lys Asp Ile Val Arg Ser Ile Ala Lys Ala Pro Gly
            100                 105                 110

Lys Arg Ala Pro Pro
        115

<210> SEQ ID NO 3
<211> LENGTH: 115
<212> TYPE: PRT
<213> ORGANISM: Human CH3/dog CH3 domain chimera

<400> SEQUENCE: 3

Ala Asp Ser Asn Pro Arg Gly Val Thr Ser Tyr Leu Ser Pro Pro Ser
 1               5                  10                  15

Pro Leu Asp Leu Tyr Ile Arg Lys Ser Pro Lys Ile Thr Cys Leu Val
            20                  25                  30

Val Asp Leu Ala Pro Ser Lys Gly Thr Val Asn Leu Thr Trp Ser Arg
            35                  40                  45

Ala Ser Gly Lys Pro Val Asn His Ser Thr Arg Lys Glu Glu Lys Gln
 50                  55                  60

Arg Asn Gly Thr Ile Thr Val Thr Ser Thr Leu Pro Val Gly Thr Arg
 65                  70                  75                  80

Asp Trp Ile Glu Gly Glu Thr Tyr Tyr Cys Arg Val Thr His Pro His
                85                  90                  95

Leu Pro Lys Asp Ile Val Arg Ser Ile Ala Lys Ala Pro Gly Lys Arg
            100                 105                 110

Ala Pro Pro
```

<210> SEQ ID NO 4
<211> LENGTH: 115
<212> TYPE: PRT
<213> ORGANISM: Human CH3

<400> SEQUENCE: 4

Ala Asp Ser Asn Pro Arg Gly Val Ser Ala Tyr Leu Ser Arg Pro Ser
 1               5                  10                  15

Pro Phe Asp Leu Phe Ile Arg Lys Ser Pro Thr Ile Cys Cys Leu Val
            20                  25                  30

Val Asp Leu Ala Pro Ser Lys Gly Thr Val Asn Leu Thr Trp Ser Arg
        35                  40                  45

Ala Ser Gly Lys Pro Val Asn His Ser Thr Arg Lys Glu Glu Lys Gln
    50                  55                  60

Arg Asn Gly Thr Leu Thr Val Thr Ser Thr Leu Pro Val Gly Thr Arg
65                  70                  75                  80

Asp Trp Ile Glu Gly Glu Thr Tyr Gln Cys Arg Val Thr His Pro His
                85                  90                  95

Leu Pro Arg Ala Leu Met Arg Ser Thr Thr Lys Thr Ser Gly Pro Arg
            100                 105                 110

Ala Ala Pro
        115

<210> SEQ ID NO 5
<211> LENGTH: 114
<212> TYPE: PRT
<213> ORGANISM: Rat CH3

<400> SEQUENCE: 5

Ser Asp Asp Glu Pro Arg Gly Val Ile Thr Tyr Leu Ile Pro Pro Ser
 1               5                  10                  15

Pro Leu Asp Leu Tyr Glu Asn Gly Thr Pro Lys Leu Thr Cys Leu Val
            20                  25                  30

Leu Asp Leu Glu Ser Glu Glu Asn Ile Thr Val Thr Trp Val Arg Glu
            35                  40                  45

Arg Lys Lys Ser Ile Gly Ser Ala Ser Gln Arg Ser Thr Lys His His
    50                  55                  60

Asn Ala Thr Thr Ser Ile Thr Ser Ile Leu Pro Val Asp Ala Lys Asp
65                  70                  75                  80

Trp Ile Glu Gly Glu Gly Tyr Gln Cys Arg Val Asp His Pro His Phe
                85                  90                  95

Pro Lys Pro Ile Val Arg Ser Ile Thr Lys Ala Pro Gly Lys Arg Ser
            100                 105                 110

Ala Pro

<210> SEQ ID NO 6
<211> LENGTH: 129
<212> TYPE: PRT
<213> ORGANISM: Baculovirus expressed human CH3 domain

<400> SEQUENCE: 6

Met Lys Phe Leu Val Asn Val Ala Leu Val Phe Met Val Val Tyr Ile
 1               5                  10                  15

Ser Tyr Ile Tyr Ala Asp Ser Asn Pro Arg Ala Val Ser Ala Tyr Leu
            20                  25                  30

-continued

```
Ser Arg Pro Ser Pro Phe Asp Leu Phe Ile Arg Lys Ser Pro Thr Ile
             35                  40                  45

Leu Cys Leu Val Leu Asp Leu Ala Pro Ser Lys Gly Thr Val Gln Leu
     50                  55                  60

Thr Trp Ser Arg Ala Ser Gly Lys Pro Val Asn His Ser Thr Arg Lys
 65                  70                  75                  80

Glu Glu Lys Gln Arg Asn Gly Thr Leu Thr Val Thr Ser Thr Leu Pro
                 85                  90                  95

Val Gly Thr Arg Asp Trp Ile Glu Gly Glu Thr Tyr Gln Cys Arg Val
            100                 105                 110

Thr His Pro His Leu Pro Arg Ala Leu Met Arg Ser Thr Thr Lys Thr
            115                 120                 125

Ser

<210> SEQ ID NO 7
<211> LENGTH: 128
<212> TYPE: PRT
<213> ORGANISM: Modified Human CH2 domain

<400> SEQUENCE: 7

Met Ser Val Pro Thr Gln Val Leu Gly Leu Leu Leu Leu Trp Leu Thr
  1               5                  10                  15

Asp Ala Arg Cys Asp Ile Val Ala Ser Arg Asp Phe Thr Pro Pro Ser
             20                  25                  30

Val Lys Ile Leu Gln Ser Ser Cys Asp Gly Gly Gly His Phe Pro Pro
             35                  40                  45

Thr Ile Gln Leu Tyr Cys Leu Val Ser Gly Tyr Thr Pro Gly Thr Ile
         50                  55                  60

Gln Ile Thr Trp Leu Glu Asp Gly Gln Val Met Asp Val Asp Leu Ser
 65                  70                  75                  80

Thr Ala Ser Thr Thr Gln Glu Gly Glu Leu Ala Ser Thr Gln Ser Glu
                 85                  90                  95

Leu Thr Leu Ser Gln Lys His Trp Leu Ser Asp Arg Thr Phe Thr Cys
            100                 105                 110

Gln Val Thr Tyr Gln Gly His Thr Phe Glu Asp Ser Thr Lys Lys Cys
            115                 120                 125

<210> SEQ ID NO 8
<211> LENGTH: 108
<212> TYPE: PRT
<213> ORGANISM: Modified Human CH4 Domain

<400> SEQUENCE: 8

Arg Ala Pro Pro Glu Val Tyr Ala Phe Ala Thr Pro Glu Trp Pro Gly
  1               5                  10                  15

Ser Arg Asp Lys Arg Thr Leu Ala Cys Leu Val Gln Asn Phe Met Pro
             20                  25                  30

Glu Asp Ile Ser Val Arg Trp Leu His Asn Glu Val Gln Leu Pro Asp
             35                  40                  45

Ala Arg His Ser Thr Thr Gln Pro Arg Lys Thr Lys Gly Ser Gly Phe
         50                  55                  60

Phe Val Phe Ser Arg Leu Ala Val Thr Arg Ala Glu Trp Gln Glu Lys
 65                  70                  75                  80

Asp Glu Phe Ile Cys Arg Ala Ile His Glu Ala Ala Ser Pro Ser Gln
                 85                  90                  95

Thr Val Gln Arg Ala Val Ser Val Asn Pro Gly Lys
            100                 105
```

<210> SEQ ID NO 9
<211> LENGTH: 236
<212> TYPE: PRT
<213> ORGANISM: Modified Human CH2-CH4 carrier protein

<400> SEQUENCE: 9

| | | | | | | | | | | | | | | | |
|---|---|---|---|---|---|---|---|---|---|---|---|---|---|---|---|
| Met | Ser | Val | Pro | Thr | Gln | Val | Leu | Gly | Leu | Leu | Leu | Trp | Leu | Thr | |
| 1 | | | | 5 | | | | | 10 | | | | | 15 | |
| Asp | Ala | Arg | Cys | Asp | Ile | Val | Ala | Ser | Arg | Asp | Phe | Thr | Pro | Pro | Ser |
| | | | 20 | | | | | 25 | | | | | 30 | | |
| Val | Lys | Ile | Leu | Gln | Ser | Ser | Cys | Asp | Gly | Gly | His | Phe | Pro | Pro | |
| | | | 35 | | | | | 40 | | | | | 45 | | |
| Thr | Ile | Gln | Leu | Tyr | Cys | Leu | Val | Ser | Gly | Tyr | Thr | Pro | Gly | Thr | Ile |
| | | 50 | | | | | 55 | | | | | 60 | | | |
| Gln | Ile | Thr | Trp | Leu | Glu | Asp | Gly | Gln | Val | Met | Asp | Val | Asp | Leu | Ser |
| 65 | | | | | 70 | | | | | 75 | | | | | 80 |
| Thr | Ala | Ser | Thr | Thr | Gln | Glu | Gly | Glu | Leu | Ala | Ser | Thr | Gln | Ser | Glu |
| | | | | 85 | | | | | 90 | | | | | 95 | |
| Leu | Thr | Leu | Ser | Gln | Lys | His | Trp | Leu | Ser | Asp | Arg | Thr | Phe | Thr | Cys |
| | | | | 100 | | | | | 105 | | | | | 110 | |
| Gln | Val | Thr | Tyr | Gln | Gly | His | Thr | Phe | Glu | Asp | Ser | Thr | Lys | Lys | Cys |
| | | | 115 | | | | | 120 | | | | | 125 | | |
| Arg | Ala | Pro | Pro | Glu | Val | Tyr | Ala | Phe | Ala | Thr | Pro | Glu | Trp | Pro | Gly |
| | | 130 | | | | | 135 | | | | | 140 | | | |
| Ser | Arg | Asp | Lys | Arg | Thr | Leu | Ala | Cys | Leu | Val | Gln | Asn | Phe | Met | Pro |
| 145 | | | | | 150 | | | | | 155 | | | | | 160 |
| Glu | Asp | Ile | Ser | Val | Arg | Trp | Leu | His | Asn | Glu | Val | Gln | Leu | Pro | Asp |
| | | | | 165 | | | | | 170 | | | | | 175 | |
| Ala | Arg | His | Ser | Thr | Thr | Gln | Pro | Arg | Lys | Thr | Lys | Gly | Ser | Gly | Phe |
| | | | 180 | | | | | 185 | | | | | 190 | | |
| Phe | Val | Phe | Ser | Arg | Leu | Ala | Val | Thr | Arg | Ala | Glu | Trp | Gln | Glu | Lys |
| | | | 195 | | | | | 200 | | | | | 205 | | |
| Asp | Glu | Phe | Ile | Cys | Arg | Ala | Ile | His | Glu | Ala | Ala | Ser | Pro | Ser | Gln |
| | | 210 | | | | | 215 | | | | | 220 | | | |
| Thr | Val | Gln | Arg | Ala | Val | Ser | Val | Asn | Pro | Gly | Lys | | | | |
| 225 | | | | | 230 | | | | | 235 | | | | | |

<210> SEQ ID NO 10
<211> LENGTH: 346
<212> TYPE: PRT
<213> ORGANISM: IgE-1 fusion protein

<400> SEQUENCE: 10

| | | | | | | | | | | | | | | | |
|---|---|---|---|---|---|---|---|---|---|---|---|---|---|---|---|
| Met | Ser | Val | Pro | Thr | Gln | Val | Leu | Gly | Leu | Leu | Leu | Trp | Leu | Thr | |
| 1 | | | | 5 | | | | | 10 | | | | | 15 | |
| Asp | Ala | Arg | Cys | Asp | Ile | Val | Ala | Ser | Arg | Asp | Phe | Thr | Pro | Pro | Ser |
| | | | 20 | | | | | 25 | | | | | 30 | | |
| Val | Lys | Ile | Leu | Gln | Ser | Ser | Cys | Asp | Gly | Gly | His | Phe | Pro | Pro | |
| | | | 35 | | | | | 40 | | | | | 45 | | |
| Thr | Ile | Gln | Leu | Tyr | Cys | Leu | Val | Ser | Gly | Tyr | Thr | Pro | Gly | Thr | Ile |
| | | 50 | | | | | 55 | | | | | 60 | | | |
| Gln | Ile | Thr | Trp | Leu | Glu | Asp | Gly | Gln | Val | Met | Asp | Val | Asp | Leu | Ser |
| 65 | | | | | 70 | | | | | 75 | | | | | 80 |
| Thr | Ala | Ser | Thr | Thr | Gln | Glu | Gly | Glu | Leu | Ala | Ser | Thr | Gln | Ser | Glu |

-continued

```
                 85                  90                  95
Leu Thr Leu Ser Gln Lys His Trp Leu Ser Asp Arg Thr Phe Thr Cys
                100                 105                 110
Gln Val Thr Tyr Gln Gly His Thr Phe Glu Asp Ser Thr Lys Lys Cys
                115                 120                 125
Ser Glu Ser Asp Pro Arg Gly Val Thr Ser Tyr Leu Ser Pro Pro Ser
            130                 135                 140
Pro Leu Asp Leu Tyr Val His Lys Ala Pro Lys Ile Thr Cys Leu Val
145                 150                 155                 160
Val Asp Leu Ala Thr Met Glu Gly Met Asn Leu Thr Trp Tyr Arg Glu
                165                 170                 175
Ser Lys Glu Pro Val Asn Pro Gly Pro Leu Asn Lys Lys Asp His Phe
                180                 185                 190
Asn Gly Thr Ile Thr Val Thr Ser Thr Leu Pro Val Asn Thr Asn Asp
            195                 200                 205
Trp Ile Glu Gly Glu Thr Tyr Tyr Cys Arg Val Thr His Pro His Leu
        210                 215                 220
Pro Lys Asp Ile Val Arg Ser Ile Ala Lys Ala Pro Gly Lys Arg Ala
225                 230                 235                 240
Pro Pro Glu Val Tyr Ala Phe Ala Thr Pro Glu Trp Pro Gly Ser Arg
                245                 250                 255
Asp Lys Arg Thr Leu Ala Cys Leu Val Gln Asn Phe Met Pro Glu Asp
            260                 265                 270
Ile Ser Val Arg Trp Leu His Asn Glu Val Gln Leu Pro Asp Ala Arg
        275                 280                 285
His Ser Thr Thr Gln Pro Arg Lys Thr Lys Gly Ser Gly Phe Phe Val
    290                 295                 300
Phe Ser Arg Leu Ala Val Thr Arg Ala Glu Trp Gln Glu Lys Asp Glu
305                 310                 315                 320
Phe Ile Cys Arg Ala Ile His Glu Ala Ala Ser Pro Ser Gln Thr Val
                325                 330                 335
Gln Arg Ala Val Ser Val Asn Pro Gly Lys
            340                 345

<210> SEQ ID NO 11
<211> LENGTH: 348
<212> TYPE: PRT
<213> ORGANISM: IgE-2 fusion protein

<400> SEQUENCE: 11

Met Ser Val Pro Thr Gln Val Leu Gly Leu Leu Leu Leu Trp Leu Thr
1               5                   10                  15
Asp Ala Arg Cys Asp Ile Val Ala Ser Arg Asp Phe Thr Pro Pro Ser
                20                  25                  30
Val Lys Ile Leu Gln Ser Ser Cys Asp Gly Gly His Phe Pro Pro
            35                  40                  45
Thr Ile Gln Leu Tyr Cys Leu Val Ser Gly Tyr Thr Pro Gly Thr Ile
        50                  55                  60
Gln Ile Thr Trp Leu Glu Asp Gly Gln Val Met Asp Val Asp Leu Ser
65                  70                  75                  80
Thr Ala Ser Thr Thr Gln Glu Gly Glu Leu Ala Ser Thr Gln Ser Glu
                85                  90                  95
Leu Thr Leu Ser Gln Lys His Trp Leu Ser Asp Arg Thr Phe Thr Cys
                100                 105                 110
```

```
Gln Val Thr Tyr Gln Gly His Thr Phe Glu Asp Ser Thr Lys Lys Cys
            115                 120                 125

Ala Asp Ser Asn Pro Arg Gly Val Ser Ala Tyr Leu Ser Arg Pro Ser
        130                 135                 140

Pro Phe Asp Leu Phe Ile Arg Lys Ser Pro Thr Ile Leu Cys Leu Val
145                 150                 155                 160

Leu Asp Leu Ala Pro Ser Lys Gly Thr Val Gln Leu Thr Trp Ser Arg
                165                 170                 175

Ala Ser Gly Lys Pro Val Asn His Ser Thr Arg Lys Glu Glu Lys Asp
            180                 185                 190

His Phe Asn Gly Thr Ile Thr Val Thr Ser Thr Leu Pro Val Asn Thr
        195                 200                 205

Asn Asp Trp Ile Glu Gly Glu Thr Tyr Tyr Cys Arg Val Thr His Pro
210                 215                 220

His Leu Pro Lys Asp Ile Val Arg Ser Ile Ala Lys Ala Pro Gly Lys
225                 230                 235                 240

Arg Ala Pro Pro Glu Val Tyr Ala Phe Ala Thr Pro Glu Trp Pro Gly
                245                 250                 255

Ser Arg Asp Lys Arg Thr Leu Ala Cys Leu Val Gln Asn Phe Met Pro
            260                 265                 270

Glu Asp Ile Ser Val Arg Trp Leu His Asn Glu Val Gln Leu Pro Asp
        275                 280                 285

Ala Arg His Ser Thr Thr Gln Pro Arg Lys Thr Lys Gly Ser Gly Phe
    290                 295                 300

Phe Val Phe Ser Arg Leu Ala Val Thr Arg Ala Glu Trp Gln Glu Lys
305                 310                 315                 320

Asp Glu Phe Ile Cys Arg Ala Ile His Glu Ala Ser Pro Ser Gln
                325                 330                 335

Thr Val Gln Arg Ala Val Ser Val Asn Pro Gly Lys
            340                 345

<210> SEQ ID NO 12
<211> LENGTH: 347
<212> TYPE: PRT
<213> ORGANISM: IgE-3 fusion protein

<400> SEQUENCE: 12

Met Ser Val Pro Thr Gln Val Leu Gly Leu Leu Leu Leu Trp Leu Thr
1               5                   10                  15

Asp Ala Arg Cys Asp Ile Val Ala Ser Arg Asp Phe Thr Pro Pro Ser
            20                  25                  30

Val Lys Ile Leu Gln Ser Ser Cys Asp Gly Gly Gly His Phe Pro Pro
        35                  40                  45

Thr Ile Gln Leu Tyr Cys Leu Val Ser Gly Tyr Thr Pro Gly Thr Ile
    50                  55                  60

Gln Ile Thr Trp Leu Glu Asp Gly Gln Val Met Asp Val Asp Leu Ser
65                  70                  75                  80

Thr Ala Ser Thr Thr Gln Glu Gly Glu Leu Ala Ser Thr Gln Ser Glu
                85                  90                  95

Leu Thr Leu Ser Gln Lys His Trp Leu Ser Asp Arg Thr Phe Thr Cys
            100                 105                 110

Gln Val Thr Tyr Gln Gly His Thr Phe Glu Asp Ser Thr Lys Lys Cys
        115                 120                 125

Ala Asp Ser Asn Pro Arg Gly Val Thr Ser Tyr Leu Ser Pro Pro Ser
    130                 135                 140
```

-continued

```
Pro Leu Asp Leu Tyr Ile Arg Lys Ser Pro Lys Ile Thr Cys Leu Val
145                 150                 155                 160

Val Asp Leu Ala Pro Ser Lys Gly Thr Val Gln Leu Thr Trp Ser Arg
            165                 170                 175

Ala Ser Gly Lys Pro Val Asn His Ser Thr Arg Lys Glu Glu Lys Gln
        180                 185                 190

Arg Asn Gly Thr Ile Thr Val Thr Ser Thr Leu Pro Val Gly Thr Arg
    195                 200                 205

Asp Trp Ile Glu Gly Glu Thr Tyr Tyr Cys Arg Val Thr His Pro His
210                 215                 220

Leu Pro Lys Asp Ile Val Arg Ser Ile Ala Lys Ala Pro Gly Lys Arg
225                 230                 235                 240

Ala Pro Pro Glu Val Tyr Ala Phe Ala Thr Pro Glu Trp Pro Gly Ser
            245                 250                 255

Arg Asp Lys Arg Thr Leu Ala Cys Leu Val Gln Asn Phe Met Pro Glu
        260                 265                 270

Asp Ile Ser Val Arg Trp Leu His Asn Glu Val Gln Leu Pro Asp Ala
    275                 280                 285

Arg His Ser Thr Thr Gln Pro Arg Lys Thr Lys Gly Ser Gly Phe Phe
290                 295                 300

Val Phe Ser Arg Leu Ala Val Thr Arg Ala Glu Trp Gln Glu Lys Asp
305                 310                 315                 320

Glu Phe Ile Cys Arg Ala Ile His Glu Ala Ala Ser Pro Ser Gln Thr
            325                 330                 335

Val Gln Arg Ala Val Ser Val Asn Pro Gly Lys
        340                 345

<210> SEQ ID NO 13
<211> LENGTH: 347
<212> TYPE: PRT
<213> ORGANISM: IgE-4 fusion protein

<400> SEQUENCE: 13

Met Ser Val Pro Thr Gln Val Leu Gly Leu Leu Leu Leu Trp Leu Thr
1               5                   10                  15

Asp Ala Arg Cys Asp Ile Val Ala Ser Arg Asp Phe Thr Pro Pro Ser
            20                  25                  30

Val Lys Ile Leu Gln Ser Ser Cys Asp Gly Gly Gly His Phe Pro Pro
        35                  40                  45

Thr Ile Gln Leu Tyr Cys Leu Val Ser Gly Tyr Thr Pro Gly Thr Ile
    50                  55                  60

Gln Ile Thr Trp Leu Glu Asp Gly Gln Val Met Asp Val Asp Leu Ser
65                  70                  75                  80

Thr Ala Ser Thr Thr Gln Glu Gly Glu Leu Ala Ser Thr Gln Ser Glu
            85                  90                  95

Leu Thr Leu Ser Gln Lys His Trp Leu Ser Asp Arg Thr Phe Thr Cys
        100                 105                 110

Gln Val Thr Tyr Gln Gly His Thr Phe Glu Asp Ser Thr Lys Lys Cys
    115                 120                 125

Ala Asp Ser Asn Pro Arg Ala Val Ser Ala Tyr Leu Ser Arg Pro Ser
130                 135                 140

Pro Phe Asp Leu Phe Ile Arg Lys Ser Pro Thr Ile Leu Cys Leu Val
145                 150                 155                 160

Leu Asp Leu Ala Pro Ser Lys Gly Thr Val Gln Leu Thr Trp Ser Arg
```

```
                165                 170                 175
Ala Ser Gly Lys Pro Val Asn His Ser Thr Arg Lys Glu Glu Lys Gln
            180                 185                 190

Arg Asn Gly Thr Leu Thr Val Thr Ser Thr Leu Pro Val Gly Thr Arg
        195                 200                 205

Asp Trp Ile Glu Gly Glu Thr Tyr Gln Cys Arg Val Thr His Pro His
    210                 215                 220

Leu Pro Arg Ala Leu Met Arg Ser Thr Thr Lys Thr Ser Gly Pro Arg
225                 230                 235                 240

Ala Ala Pro Glu Val Tyr Ala Phe Ala Thr Pro Glu Trp Pro Gly Ser
                245                 250                 255

Arg Asp Lys Arg Thr Leu Ala Cys Leu Val Gln Asn Phe Met Pro Glu
            260                 265                 270

Asp Ile Ser Val Arg Trp Leu His Asn Glu Val Gln Leu Pro Asp Ala
        275                 280                 285

Arg His Ser Thr Thr Gln Pro Arg Lys Thr Lys Gly Ser Gly Phe Phe
    290                 295                 300

Val Phe Ser Arg Leu Ala Val Thr Arg Ala Glu Trp Gln Glu Lys Asp
305                 310                 315                 320

Glu Phe Ile Cys Arg Ala Ile His Glu Ala Ala Ser Pro Ser Gln Thr
                325                 330                 335

Val Gln Arg Ala Val Ser Val Asn Pro Gly Lys
            340                 345

<210> SEQ ID NO 14
<211> LENGTH: 346
<212> TYPE: PRT
<213> ORGANISM: IgE-5 fusion protein

<400> SEQUENCE: 14

Met Ser Val Pro Thr Gln Val Leu Gly Leu Leu Leu Leu Trp Leu Thr
 1               5                  10                  15

Asp Ala Arg Cys Asp Ile Val Ala Ser Arg Asp Phe Thr Pro Pro Ser
            20                  25                  30

Val Lys Ile Leu Gln Ser Ser Cys Asp Gly Gly Gly His Phe Pro Pro
        35                  40                  45

Thr Ile Gln Leu Tyr Cys Leu Val Ser Gly Tyr Thr Pro Gly Thr Ile
    50                  55                  60

Gln Ile Thr Trp Leu Glu Asp Gly Gln Val Met Asp Val Asp Leu Ser
65                  70                  75                  80

Thr Ala Ser Thr Thr Gln Glu Gly Glu Leu Ala Ser Thr Gln Ser Glu
                85                  90                  95

Leu Thr Leu Ser Gln Lys His Trp Leu Ser Asp Arg Thr Phe Thr Cys
            100                 105                 110

Gln Val Thr Tyr Gln Gly His Thr Phe Glu Asp Ser Thr Lys Lys Cys
        115                 120                 125

Ser Asp Asp Glu Pro Arg Gly Val Ile Thr Tyr Leu Ile Pro Pro Ser
    130                 135                 140

Pro Leu Asp Leu Tyr Glu Asn Gly Thr Pro Lys Leu Thr Cys Leu Val
145                 150                 155                 160

Leu Asp Leu Glu Ser Glu Glu Asn Ile Thr Val Thr Trp Val Arg Glu
                165                 170                 175

Arg Lys Lys Ser Ile Gly Ser Ala Ser Gln Arg Ser Thr Lys His His
            180                 185                 190
```

```
Asn Ala Thr Thr Ser Ile Thr Ser Ile Leu Pro Val Asp Ala Lys Asp
            195                 200                 205

Trp Ile Glu Gly Glu Gly Tyr Gln Cys Arg Val Asp His Pro His Phe
        210                 215                 220

Pro Lys Pro Ile Val Arg Ser Ile Thr Lys Ala Pro Gly Lys Arg Ser
225                 230                 235                 240

Ala Pro Glu Val Tyr Ala Phe Ala Thr Pro Glu Trp Pro Gly Ser Arg
                245                 250                 255

Asp Lys Arg Thr Leu Ala Cys Leu Val Gln Asn Phe Met Pro Glu Asp
            260                 265                 270

Ile Ser Val Arg Trp Leu His Asn Glu Val Gln Leu Pro Asp Ala Arg
        275                 280                 285

His Ser Thr Thr Gln Pro Arg Lys Thr Lys Gly Ser Gly Phe Phe Val
    290                 295                 300

Phe Ser Arg Leu Ala Val Thr Arg Ala Glu Trp Gln Glu Lys Asp Glu
305                 310                 315                 320

Phe Ile Cys Arg Ala Ile His Glu Ala Ala Ser Pro Ser Gln Thr Val
                325                 330                 335

Gln Arg Ala Val Ser Val Asn Pro Gly Lys
            340                 345

<210> SEQ ID NO 15
<211> LENGTH: 342
<212> TYPE: DNA
<213> ORGANISM: Dog CH3 domain

<400> SEQUENCE: 15
tcagagtccg accccgagg cgtgacgagc tacctgagcc cacccagccc ccttgacctg      60
tatgtccaca aggcgcccaa gatcacctgc ctggtagtgg acctggccac catggaaggc     120
atgaacctga cctggtaccg ggagagcaaa gaacccgtga accgggcccc tttgaacaag     180
aaggatcact tcaatgggac gatcacagtc acgtctaccc tgccagtgaa caccaatgac     240
tggatcgagg gcgagaccta ctattgcagg gtgacccacc cgcacctgcc caaggacatc     300
gtgcgctcca ttgccaaggc ccctggcaag cgtgcccccc cg                       342

<210> SEQ ID NO 16
<211> LENGTH: 355
<212> TYPE: DNA
<213> ORGANISM: Human/dog CH3 domain fusion

<400> SEQUENCE: 16
gcagattcca acccgagagg ggtgagcgcc tacctaagcc ggcccagccc gttcgacctg      60
ttcatccgca agtcgcccac gatcacctgt ctggtggtgg acctggcacc cagcaagggg     120
accgtgaacc tgacctggtc ccgggccagt gggaagcctg tgaaccactc caccagaaag     180
gaggagaaga aggatcactt caatgggacg atcacagtca cgtctaccct gccagtgaac     240
accaatgact ggatcgaggg cgagacctac tattgcaggg tgacccaccc gcacctgccc     300
aaggacatcg tgcgctccat tgccaaggcc cctggcaagc gtgcccccc ggaag          355

<210> SEQ ID NO 17
<211> LENGTH: 345
<212> TYPE: DNA
<213> ORGANISM: Human/dog CH3 domain chimera

<400> SEQUENCE: 17
gcagattcca acccgagagg ggtgaccagc tacctaagcc cgcccagccc gctggacctg      60
```

```
tacatccgca agtcgcccaa gatcacctgt ctggtggtgg acctggcacc cagcaagggg      120
accgtgaacc tgacctggtc ccgggccagt gggaagcctg tgaaccactc caccagaaag      180
gaggagaagc aacggaatgg gacgatcaca gtcacgtcta ccctgccagt gggcaccaga      240
gactggatcg agggcgagac ctactattgc agggtgaccc acccgcacct gcccaaggac      300
atcgtgcgct ccattgccaa ggcccctggc aagcgtgccc cccg                      345

<210> SEQ ID NO 18
<211> LENGTH: 345
<212> TYPE: DNA
<213> ORGANISM: Human CH3 domain

<400> SEQUENCE: 18
gcagattcca acccgagagg ggtgagcgcc tacctaagcc ggcccagccc gttcgacctg      60
ttcatccgca agtcgcccac gatcacctgt ctggtggtgg acctggcacc cagcaagggg      120
accgtgaacc tgacctggtc ccgggccagt gggaagcctg tgaaccactc caccagaaag      180
gaggagaagc agcgcaatgg cacgttaacc gtcacgtcca ccctgccggt gggcacccga      240
gactggatcg aggggggagac ctaccagtgc agggtgaccc accccacct gcccagggcc      300 ctcatgcggt ccacgaccaa gaccagcggc ccgcgtgctg ccccg                     345

<210> SEQ ID NO 19
<211> LENGTH: 342
<212> TYPE: DNA
<213> ORGANISM: Rat CH3 domain

<400> SEQUENCE: 19
tcagatgatg agccccgggg tgtgattacc tacctgatcc cacccagtcc cctcgacctg      60
tatgaaaatg ggactcccaa acttacctgt ctggttttgg acctggaaag tgaggagaat      120
atcaccgtga cgtgggtccg agagcgtaag aagtctatag gttcggcatc ccagaggagt      180
accaagcacc ataatgccac aaccagtatc acctccatct tgccagtgga tgccaaggac      240
tggatcgaag gtgaaggcta ccagtgcaga gtggaccacc ctcactttcc caagcccatt      300
gtgcgttcca tcaccaaggc cccaggcaag cgctcagccc ca                        342

<210> SEQ ID NO 20
<211> LENGTH: 327
<212> TYPE: DNA
<213> ORGANISM: Human CH3 domain (baculovirus expressed)

<400> SEQUENCE: 20
gacagcaacc cgagagggggt gagcgcctac ctaagccggc ccagcccgtt cgacctgttc      60
atccgcaagt cgcccacgat cacctgtctg gtggtggacc tggcacccag caagggggacc      120 gtgaacctga cctggtcccg ggccagtggg aagcctgtga accactccac cagaaaggag      180
gagaagcagc gcaatggcac gttaaccgtc acgtccaccc tgccggtggg cacccgagac      240
tggatcgagg gggagaccta ccagtgcagg gtgacccacc ccacctgcc cagggccctc      300 atgcggtcca cgaccaagac ctcctga                                         327

<210> SEQ ID NO 21
<211> LENGTH: 384
<212> TYPE: DNA
<213> ORGANISM: Modified human CH2 domain

<400> SEQUENCE: 21
```

-continued

| | |
|---|---|
| atgagtgtgc ccactcaggt cctggggttg ctgctgctgt ggcttacaga tgccagatgt | 60 |
| gacatcgtcg cctccaggga cttcacccecg ccctccgtga agatcttaca gtcgtcctgc | 120 |
| gacggcggcg ggcacttccc cccgaccatc cagctctact gcctcgtctc tgggtacacc | 180 |
| ccagggacta tccagatcac ctggctggag gacgggcagg tcatggacgt ggacttgtcc | 240 |
| accgcctcta ccacgcagga gggtgagctg cctccacac aaagcgagct caccctcagc | 300 |
| cagaagcact ggctgtcaga ccgcaccttc acctgccagg tcacctatca aggtcacacc | 360 |
| tttgaggaca gcaccaagaa gtgt | 384 |

<210> SEQ ID NO 22
<211> LENGTH: 315
<212> TYPE: DNA
<213> ORGANISM: Modified human CH4 domain

<400> SEQUENCE: 22

| | |
|---|---|
| gaagtctatg cgtttgcgac gccggagtgg ccggggagcc gggacaagcg cacccctcgcc | 60 |
| tgcctggtgc agaacttcat gcctgaggac atctcggtgc gctggctgca acgagggtg | 120 |
| cagctccccgg acgccggca cagcacgacg cagccccgca agaccaaggg ctccggcttc | 180 |
| ttcgtcttca gccgcctggc ggtgaccagg gccgaatggc aggagaaaga tgagttcatc | 240 |
| tgccgtgcag tccatgaggc agcgagcccc tcacagaccg tccagcgagc ggtgtctgta | 300 |
| aatcccggta aatga | 315 |

<210> SEQ ID NO 23
<211> LENGTH: 699
<212> TYPE: DNA
<213> ORGANISM: Modified human CH2-CH4 carrier

<400> SEQUENCE: 23

| | |
|---|---|
| atgagtgtgc ccactcaggt cctggggttg ctgctgctgt ggcttacaga tgccagatgt | 60 |
| gacatcgtcg cctccaggga cttcacccecg ccctccgtga agatcttaca gtcgtcctgc | 120 |
| gacggcggcg ggcacttccc cccgaccatc cagctctact gcctcgtctc tgggtacacc | 180 |
| ccagggacta tccagatcac ctggctggag gacgggcagg tcatggacgt ggacttgtcc | 240 |
| accgcctcta ccacgcagga gggtgagctg cctccacac aaagcgagct caccctcagc | 300 |
| cagaagcact ggctgtcaga ccgcaccttc acctgccagg tcacctatca aggtcacacc | 360 |
| tttgaggaca gcaccaagaa gtgtgaagtc tatgcgtttg cgacgccgga gtggccgggg | 420 |
| agcccgggaca agcgcaccct cgcctgcctg gtgcagaact tcatgcctga ggacatctcg | 480 |
| gtgcgctggc tgcacaacga ggtgcagctc ccggacgccc ggcacagcac gacgcagccc | 540 |
| cgcaagacca agggctccgg cttcttcgtc ttcagccgcc tggcggtgac cagggccgaa | 600 |
| tggcaggaga agatgagtt catctgccgt gcagtccatg aggcagcgag ccctcacag | 660 |
| accgtccagc gagcggtgtc tgtaaatccc ggtaaatga | 699 |

<210> SEQ ID NO 24
<211> LENGTH: 1041
<212> TYPE: DNA
<213> ORGANISM: IgE-1 construct

<400> SEQUENCE: 24

| | |
|---|---|
| atgagtgtgc ccactcaggt cctggggttg ctgctgctgt ggcttacaga tgccagatgt | 60 |
| gacatcgtcg cctccaggga cttcacccecg ccctccgtga agatcttaca gtcgtcctgc | 120 |
| gacggcggcg ggcacttccc cccgaccatc cagctctact gcctcgtctc tgggtacacc | 180 |

```
ccagggacta tccagatcac ctggctggag gacgggcagg tcatggacgt ggacttgtcc      240
accgcctcta ccacgcagga gggtgagctg gcctccacac aaagcgagct cacccctcagc     300 cagaagcact ggctgtcaga ccgcaccttc acctgccagg tcacctatca aggtcacacc      360
tttgaggaca gcaccaagaa gtgttcagag tccgaccccc gaggcgtgac gagctacctg      420
agcccaccca gccccttga cctgtatgtc acaaggcgc ccaagatcac ctgcctggta        480
gtggacctgg ccaccatgga aggcatgaac ctgacctggt accgggagag caaagaaccc     540
gtgaacccgg gcccttttgaa caagaaggat cacttcaatg gacgatcac agtcacgtct     600 accctgccag tgaacaccaa tgactggatc gagggcgaga cctactattg cagggtgacc    660
cacccgcacc tgcccaagga catcgtgcgc tccattgcca aggcccctgg caagcgtgcc   720 ccccggaag tctatgcgtt tgcgacgccg gagtggccgg ggagccggga caagcgcacc    780
ctcgcctgcc tggtgcagaa cttcatgcct gaggacatct cggtgcgctg gctgcacaac    840
gaggtgcagc tcccggacgc ccggcacagc acgacgcagc ccgcaagac caagggctcc    900 ggcttcttcg tcttcagccg cctggcggtg accagggccg aatggcagga gaaagatgag   960
ttcatctgcc gtgcagtcca tgaggcagcg agcccctcac agaccgtcca gcgagcggtg  1020 tctgtaaaatc ccggtaaatg a                                              1041

<210> SEQ ID NO 25
<211> LENGTH: 1050
<212> TYPE: DNA
<213> ORGANISM: IgE-2 construct

<400> SEQUENCE: 25
atgagtgtgc ccactcaggt cctggggttg ctgctgctgt ggcttacaga tgccagatgt      60
gacatcgtcg cctccaggga cttcaccccg ccctccgtga agatcttaca gtcgtcctgc    120
gacggcggcg ggcacttccc cccgaccatc cagctctact gcctcgtctc tgggtacacc    180
ccagggacta tccagatcac ctggctggag gacgggcagg tcatggacgt ggacttgtcc    240
accgcctcta ccacgcagga gggtgagctg gcctccacac aaagcgagct cacccctcagc   300 cagaagcact ggctgtcaga ccgcaccttc acctgccagg tcacctatca aggtcacacc    360
tttgaggaca gcaccaagaa gtgtgcagat tccaacccga gggggtgag cgcctaccta    420 agccggccca gccgttcga cctgttcatc cgcaagtcgc ccacgatcac ctgtctggtg   480
gtggacctgg cacccagcaa ggggaccgtg aacctgacct ggtcccgggc cagtgggaag   540
cctgtgaacc actccaccag aaaggaggag aagaaggatc acttcaatgg gacgatcaca   600
gtcacgtcta ccctgccagt gaacaccaat gactggatcg agggcgagac ctactattgc   660
agggtgaccc acccgcacct gcccaaggac atcgtgcgct ccattgccaa ggcccctggc   720
aagcgtgccc cccggaagt ctatgcgttt gcgacgccgg agtggccggg gagccgggac    780
aagcgcaccc tcgcctgcct ggtgcagaac ttcatgcctg aggacatctc ggtgcgctgg   840
ctgcacaacg aggtgcagct cccggacgcc cggcacagca cgacgcagcc cgcaagacc    900 aagggctccg gcttcttcgt cttcagccgc ctggcggtga ccaggccga atggcaggag    960 aaagatgagt tcatctgccg tgcagtccat gaggcagcga gccctcaca gaccgtccag   1020 cgagcggtgt ctgtaaatcc cggtaaatga                                     1050

<210> SEQ ID NO 26
<211> LENGTH: 1044
<212> TYPE: DNA
```

<213> ORGANISM: IgE-3 construct

<400> SEQUENCE: 26

| | | | | | |
|---|---|---|---|---|---|
| atgagtgtgc | ccactcaggt | cctggggttg | ctgctgctgt | ggcttacaga | tgccagatgt | 60 |
| gacatcgtcg | cctccaggga | cttcaccccg | ccctccgtga | agatcttaca | gtcgtcctgc | 120 |
| gacggcggcg | ggcacttccc | cccgaccatc | cagctctact | gcctcgtctc | tgggtacacc | 180 |
| ccagggacta | tccagatcac | ctggctggag | gacgggcagg | tcatggacgt | ggacttgtcc | 240 |
| accgcctcta | ccacgcagga | gggtgagctg | gcctccacac | aaagcgagct | caccctcagc | 300 |
| cagaagcact | ggctgtcaga | ccgcaccttc | acctgccagg | tcacctatca | aggtcacacc | 360 |
| tttgaggaca | gcaccaagaa | gtgtgcagat | tccaacccga | gagggtgac | cagctaccta | 420 |
| agcccgccca | gcccgctgga | cctgtacatc | cgcaagtcgc | ccaagatcac | ctgtctggtg | 480 |
| gtggacctgg | cacccagcaa | ggggaccgtg | aacctgacct | ggtcccgggc | cagtgggaag | 540 |
| cctgtgaacc | actccaccag | aaaggaggag | aagcaacgga | atgggacgat | cacagtcacg | 600 |
| tctaccctgc | cagtgggcac | cagagactgg | atcgagggcg | agacctacta | ttgcagggtg | 660 |
| acccaccgc | acctgcccaa | ggacatcgtg | cgctccattg | ccaaggcccc | tggcaagcgt | 720 |
| gccccccccgg | aagtctatgc | gtttgcgacg | ccggagtggc | cggggagccg | ggacaagcgc | 780 |
| accctcgcct | gcctggtgca | gaacttcatg | cctgaggaca | tctcggtgcg | ctggctgcac | 840 |
| aacgaggtgc | agctcccgga | cgcccggcac | agcacgacgc | agcccgcaa | gaccaagggc | 900 |
| tccggcttct | tcgtcttcag | ccgcctggcg | gtgaccaggg | ccgaatggca | ggagaaagat | 960 |
| gagttcatct | gccgtgcagt | ccatgaggca | gcgagcccct | cacagaccgt | ccagcgagcg | 1020 |
| gtgtctgtaa | atcccggtaa | atga | | | | 1044 |

<210> SEQ ID NO 27
<211> LENGTH: 1044
<212> TYPE: DNA
<213> ORGANISM: IgE-4 construct

<400> SEQUENCE: 27

| | | | | | |
|---|---|---|---|---|---|
| atgagtgtgc | ccactcaggt | cctggggttg | ctgctgctgt | ggcttacaga | tgccagatgt | 60 |
| gacatcgtcg | cctccaggga | cttcaccccg | ccctccgtga | agatcttaca | gtcgtcctgc | 120 |
| gacggcggcg | ggcacttccc | cccgaccatc | cagctctact | gcctcgtctc | tgggtacacc | 180 |
| ccagggacta | tccagatcac | ctggctggag | gacgggcagg | tcatggacgt | ggacttgtcc | 240 |
| accgcctcta | ccacgcagga | gggtgagctg | gcctccacac | aaagcgagct | caccctcagc | 300 |
| cagaagcact | ggctgtcaga | ccgcaccttc | acctgccagg | tcacctatca | aggtcacacc | 360 |
| tttgaggaca | gcaccaagaa | gtgtgcagat | tccaacccga | gagggtgag | cgcctaccta | 420 |
| agccggccca | gcccgttcga | cctgttcatc | cgcaagtcgc | ccacgatcac | ctgtctggtg | 480 |
| gtggacctgg | cacccagcaa | ggggaccgtg | aacctgacct | ggtcccgggc | cagtgggaag | 540 |
| cctgtgaacc | actccaccag | aaaggaggag | aagcagcgca | atggcacgtt | aaccgtcacg | 600 |
| tccaccctgc | cggtgggcac | ccgagactgg | atcgaggggg | agacctacca | gtgcagggtg | 660 |
| acccaccccc | acctgcccag | ggccctcatg | cggtccacga | ccaagaccag | cggcccgcgt | 720 |
| gctgccccgg | aagtctatgc | gtttgcgacg | ccggagtggc | cggggagccg | ggacaagcgc | 780 |
| accctcgcct | gcctggtgca | gaacttcatg | cctgaggaca | tctcggtgcg | ctggctgcac | 840 |
| aacgaggtgc | agctcccgga | cgcccggcac | agcacgacgc | agcccgcaa | gaccaagggc | 900 |
| tccggcttct | tcgtcttcag | ccgcctggcg | gtgaccaggg | ccgaatggca | ggagaaagat | 960 |

```
gagttcatct gccgtgcagt ccatgaggca gcgagcccct cacagaccgt ccagcgagcg   1020
gtgtctgtaa atcccggtaa atga                                          1044

<210> SEQ ID NO 28
<211> LENGTH: 1041
<212> TYPE: DNA
<213> ORGANISM: IgE-5 construct

<400> SEQUENCE: 28
atgagtgtgc ccactcaggt cctggggttg ctgctgctgt ggcttacaga tgccagatgt     60
gacatcgtcg cctccaggga cttcaccccg ccctccgtga agatcttaca gtcgtcctgc   120
gacggcggcg ggcacttccc cccgaccatc cagctctact gcctcgtctc tgggtacacc   180
ccagggacta tccagatcac ctggctggag gacgggcagg tcatggacgt ggacttgtcc   240
accgcctcta ccacgcagga gggtgagctg gcctccacac aaagcgagct caccctcagc   300
cagaagcact ggctgtcaga ccgcaccttc acctgccagg tcacctatca aggtcacacc   360
tttgaggaca gcaccaagaa gtgctcagat gatgagcccc ggggtgtgat tacctacctg   420
atcccaccca gtcccctcga cctgtatgaa aatgggactc ccaaacttac ctgtctggtt   480
ttggacctgg aaagtgagga gaatatcacc gtgacgtggg tccgagagcg taagaagtct   540
ataggttcgg catcccagag gagtaccaag caccataatg ccacaaccag tatcacctcc   600
atcttgccag tggatgccaa ggactggatc gaaggtgaag gctaccagtg cagagtggac   660
caccctcact ttcccaagcc cattgtgcgt tccatcacca aggccccagg caagcgctca   720
gccccagaag tctatgcgtt tgcgacgccg gagtggccgg ggagccggga caagcgcacc   780
ctcgcctgcc tggtgcagaa cttcatgcct gaggacatct cggtgcgctg gctgcacaac   840
gaggtgcagc tcccggacgc ccggcacagc acgacgcagc cccgcaagac caagggctcc   900
ggcttcttcg tcttcagccg cctggcggtg accagggccg aatggcagga aaagatgag   960 ttcatctgcc gtgcagtcca tgaggcagcg agccctcac agaccgtcca gcgagcggtg  1020
tctgtaaatc ccggtaaatg a                                             1041
```

NON-ANAPHYLACTOGENIC IGE FUSION PROTEINS

CROSS REFERENCE TO RELATED APPLICATION

The present application claims the benefit of U.S. Provisional Application 60/292,638 filed May 22. 2001.

FIELD OF THE INVENTION

The present invention relates to compositions and methods for the use of antigenic peptides derived from the Fc portion of the epsilon heavy chain of IgE molecules as vaccines for the treatment and prevention of IgE-mediated allergic disorders. In particular, the present invention relates to compositions comprising at least one antigenic peptide comprising an amino acid sequence derived from the CH3 domain of IgE molecules from two different species for the treatment or prevention of an IgE-mediated allergic disorder. The present invention also relates to compositions comprising antigenic peptides coupled to heterologous carrier proteins and optionally further comprising an adjuvant. The compositions of the present invention induce anti-IgE antibodies which bind to soluble (free) IgE in serum and other bodily fluids, prevent IgE from binding to its high affinity receptors on mast cells and basophils, and do not cross-link receptor-bound IgE. The present invention further relates to methods of administering compositions of the invention to animals, preferably mammals and most preferably humans, for the treatment or prevention of IgE-mediated allergic disorders.

BACKGROUND OF THE INVENTION

Immune-mediated allergic (hypersensitivity) reactions are classified into four types (I–IV) according to the underlying mechanisms leading to the expression of the allergic symptoms. Type I allergic reactions are characterized by IgE-mediated release of vasoactive substances such as histamine from mast cells and basophils. The release of these substances and the subsequent manifestation of allergic symptoms are initiated by the cross-linking of allergen-bound IgE to its receptor on the surface of mast cells and basophils.

An IgE antibody is a complex molecule consisting of two identical heavy chains and two identical light chains held together by disulfide bonds in a "Y" shape-configuration. Each light chain consists of a variable ($V_L$) domain linked to a constant domain ($C_L$), and each heavy chain consists of a variable domain ($V_H$) and four constant domains (CH1, CH2, CH3, and CH4, also known as C$\epsilon$1, C$\epsilon$2, C$\epsilon$3, and C$\epsilon$4; respectively). The two arms of an IgE antibody contain the site at which an IgE antibody binds to its specific antigen (allergen) and each arm is referred to as a Fab (fragment-antigen-binding) fragment. The tail of an IgE antibody is termed Fc (fragment-crystalline) as it can form crystals when separated from the Fab fragments of the antibody under appropriate experimental conditions. The Fc fragment of an IgE antibody consists of the CH2, CH3, and CH4 domains and contains the biologically active structures of the IgE antibody (e.g., receptor binding sites).

The production of IgE antibodies requires interactions and collaborations among three cells; antigen presenting cells (APC), T lymphocytes (T helper cells; Th) and antibody producing cells (B lymphocytes; B cells). When a foreign substance, an allergen, is introduced for the first time into the body of subjects (e.g., by inhalation of environmental allergen, ingestion of certain foods, or via the skin), the allergen is taken up by APC's (e.g., macrophages) which then digest or process the allergen into smaller fragments (epitopes). These fragments are displayed on the surface of APC's in association with specific molecules known as major histocompatibility complex proteins. The allergen fragment/MHC complex displayed on the surface of APC's is recognized and bound by receptors on the surface of specific T lymphocytes. This recognition and binding event leads to the activation of T lymphocytes and the subsequent expression and secretion of cytokines such as interleukin-4 (IL-4). These cytokines induce the multiplication, clonal expansion and differentiation of B cells specific for the allergen in question (i.e., B cell which express on their surface immunoglobulin receptors capable of binding to the allergen) and ultimately lead to the production of IgE antibodies from these B cells. A portion of the activated T lymphocytes and IgE producing B cells eventually become committed to a pool of cells called T and B memory cells, which are capable of faster recognition of allergen upon subsequent exposure to the allergen.

In individuals suffering from type I allergic reactions, exposure to an allergen for a second time leads to the production of high levels of IgE antibodies specific for the allergen as a result of the involvement of memory B and T cells in the 3-cell interaction required for IgE production. The high levels of IgE antibodies produced cause an increase in the cross-linking of IgE receptors on mast cells and basophils by allergen-bound IgE, which in turn leads to the activation of these cells and the release of the pharmacological mediators that are responsible for the clinical manifestations of type I allergic diseases.

Two receptors with differing affinities for IgE have been identified and characterized. The high affinity receptor (Fc$\epsilon$RI) is expressed on the surface of mast cells and basophils. The low affinity receptor (Fc$\epsilon$RII/CD23) is expressed on many cell types including B cells, T cells, macrophages, eosinophils and Langerhan cells. The high affinity IgE receptor consists of three subunits (alpha, beta and gamma chains). Several studies demonstrate that only the alpha chain is involved in the binding of IgE, whereas the beta and gamma chains (which are either transmembrane or cytoplasmic proteins) are required for signal transduction events. The identification of IgE structures required for IgE to bind to the Fc$\epsilon$RI on mast cells and basophils is of utmost importance in devising strategies for treatment or prevention of IgE-mediated allergies. For example, the elucidation of the IgE receptor-binding site could lead to the identification of peptides or small molecules that block the binding of IgE to receptor-bearing cells in vivo.

Over the last 15 years, a variety of approaches have been utilized to determine the Fc$\epsilon$RI binding site on IgE. These approaches can be classified into five different categories. In one approach, small peptides corresponding to portions of the Fc part of an IgE molecule were produced and analyzed for their ability to inhibit IgE from its receptors. See, for example, Nakamura et al., EP0263655 published Apr. 13, 1988, Burt et al., 1987, European Journal of Immunol., 17:437–440; Helm et al., 1988, Nature 331:180–183; Helm et al., 1989, PNAS 86:9465–9469; Vercelli et al., 1989, Nature 338:649–651; Nio et al., 1990, Peptide Chemistry, 2: 203–208; Nio et al., 1993, FEBS Lett. 319:225–228; and Nio et al., 1992, FEBS Lett. 314:229–231. Although many of the peptides described in these studies were shown to inhibit the binding of IgE to its receptors, different studies reported different sequences as being responsible for IgE binding.

Helm et al. (1988, Nature 331:180–183) identified a 75 amino acid peptide that spans the junction between CH2 and CH3 domains of IgE and showed that this peptide binds to the IgE receptor with an affinity close to that of the native IgE molecule. On the other hand, Basu et al. (1993, Journal of Biological Chemistry 268: 13118–13127) expressed various fragments from IgE molecules and found that only those fragments containing both the CH3 and CH4 domains were able to bind IgE and that CH2 domain is not necessary for binding. Vangelista et al. (1999, Journal of Clinical Investigation 103:1571–1578) expressed only the CH3 domain of IgE and showed that this domain alone could bind to IgE receptor and prevent binding of IgE to its receptor. The results of Basu et al. and Vangelista et al. are inconsistent and conflict with those of Helm et al. cited above.

In a second approach to identify the FcεRI binding site on IgE, polyclonal antibodies against peptides corresponding to parts of the CH2 domain, CH3 domain or CH4 domain were produced and used to probe for receptor binding site on IgE (Robertson et al., 1988, Molecular Immunol. 25:103–118). Robertson et al. concluded that the amino acid residues defined by a peptide derived from the CH4 domain were not likely to be involved in receptor binding, whereas amino acid residues defined by a peptide derived from the CH3 domain of IgE were most likely proximal to the IgE receptor-binding site (amino acids 387–401). However, the anti-CH3 peptide antibodies induced in response to the CH3 peptide released histamine from IgE-loaded mast cells indicating that the amino acids defined by the CH3 peptide did not define the bona fide IgE receptor-binding site and that anti-CH3 peptide antibodies could cause anaphylaxis.

In a third approach to identify the FcεRI binding site on IgE, several investigators produced IgE mutants in an attempt to identify the amino acid residues involved in receptor binding (see, e.g., Schwarzbaum et al., 1989, European Journal of Immunology 19:1015–1023; Weetall et al., 1990, Journal of Immunology 145:3849–3854; and Presta et al., 1994, Journal of Biological Chemistry 269:26368–26373). Schwartzbaum et al. demonstrated that an IgE antibody with the point mutation proline to histidine at amino acid residue 442 in the CH4 domain has a two fold reduced affinity for the IgE receptor. Schwartzbaum et al. concluded that the CH4 domain of an IgE antibody is involved in IgE binding to its receptor. However, Schwartzbaum's conclusion contradict Weetall et al.'s conclusion that the binding of IgE to its high affinity receptor involves portions of the CH2 and CH3 domains of the IgE antibody, but not the CH4 domain. Further, Schwartzbaum et al.'s conclusions contradict Presta et al.'s conclusion that the amino acid residues of the IgE antibody important for binding to the FcεRI are located in the CH3 domain.

In a fourth approach to identify the FcεRI binding site on IgE, chimeric IgE molecules were constructed and analyzed for their ability to bind to the FcεRI. Weetall et al., supra constructed a series of chimeric murine IgE-human IgG molecules and tested their binding to the IgE receptor. Weetall et al., supra concluded that the CH4 domain does not participate in receptor binding and that the CH2 and CH3 domains are both required for binding to the high affinity receptor on mast cells. In another study, Nissim et al. (1993, Journal of Immunol 150:1365–1374) tested the ability of a series of human IgE-murine IgE chimera to bind to the FcεRI and concluded that only the CH3 domain is needed for binding to the FcεRI. The conclusion by Nissim et al. corroborates the conclusion by Vangelista et al. that the CH3 domain of IgE alone binds to the FcεRI. However, the conclusions by Nissim et al. and Vangelista et al. contradict the conclusions of Weetall et al. and Robertson et al.

Presta et al., supra produced chimeric human IgG in which the CγH2 was replaced with CH3 from human IgE. When tested for receptor binding, this chimera bound to the FcεRI albeit with a four-fold reduced affinity compared with native IgE. The results of Presta et al. appear to corroborate with the results of Nissim et al., but conflict with those of Weetall et al., Helm et al., and Basu et. al., cited above. In a further attempt to define the exact amino acid residues responsible for the binding of IgE to its receptor, Presta et al. inserted specific amino acid residues corresponding to CH2–CH3 hinge region and three loops from the CH3 domain of human IgE into their analogous locations within human IgG and called these mutants IgGEL. Unfortunately, when these IgGEL variants were tested for receptor binding, they exhibited minimal binding compared to the native IgE or the IgG in which the full length IgE CH3 domain replaced the full length CγH2 domain. In a fifth approach to identify the FcεRI binding site on IgE, monoclonal antibodies have been developed and analyzed for their ability to block IgE binding to the FcεRI. See, for example, Del Prado et al., 1991, Molecular Immunology 28:839–844; Keegan et al., 1991, Molecular Immunology 28:1149–1154; Hook et al., 1991, Molecular Immunology 28:631–639; Takemoto et al., 1994, Microbiology and Immunology 38:63–71; and Baniyash et al., 1988, Molecular Immunology 25:705–711. Although many monoclonal antibodies have been developed, they have provided little information on the bona fide IgE receptor-binding site because in many cases the amino acid sequence recognized by these monoclonal antibodies have not or could not be identified. Further, the monoclonal antibodies developed may block IgE from binding to its receptor by steric hindrance or induction of severe conformational changes in the IgE molecule, rather than by the binding and masking of IgE residues directly involved in receptor binding.

It is apparent from the above discussion that approaches that have been devised to identify the receptor binding site on IgE have produced conflicting results. The difficulty in the identification of the amino acid residues of IgE responsible for receptor binding could be further complicated by the possibility that the site on IgE used for binding to the receptor may not be a linear sequence of amino acids, which could be mimicked by a synthetic peptide. Rather, the binding site may be a conformational determinant formed by multiple amino acids that are far apart in the IgE protein sequence which are brought into close proximity only in the native three-dimensional structure of IgE. Studies with IgE variants, IgE chimera, and monoclonal anti-IgE antibodies strongly suggest that the binding site is a conformational determinant.

Currently, IgE-mediated allergic reactions are treated with drugs such as antihistamines and corticosteroids which attempt to alleviate the symptoms associated with allergic reactions by counteracting the effects of the vasoactive substances released from mast cells and basophils. High doses of antihistamines and corticosteroids have deleterious side effects such as renal and gastrointestinal toicities. Thus, other methods for treating type I allergic reactions are needed.

One approach to the treatment of type I allergic disorders has been the production of monoclonal antibodies which react with soluble (free) IgE in serum, block IgE from binding to its receptor on mast cells and basophils, and do not bind to receptor-bound IgE (i.e., they are non-anaphylactogenic). Two such monoclonal antibodies (rhuMab E25 and CGP56901) are in advanced stages of clinical development for treatment of IgE-mediated allergic reactions (see, e.g., Chang, T. W., 2000, Nature Biotechnology 18:157–62). The identity of the amino acid residues of the IgE molecule recognized by these monoclonal antibodies are not known and it is presumed that these monoclonal antibodies recognize conformational determinants on IgE.

Although early results from clinical trials with therapeutic anti-IgE monoclonal antibodies suggest that these therapies are effective in the treatment of atopic allergies, the use of monoclonal antibodies for long-term treatment of allergies has some significant shortcomings. First, since these monoclonal antibodies were originally produced in mice, they had to be reengineered so as to replace mouse sequences with consensus human IgG sequences (Presta et al., 1993, The Journal of Immunology 151:2623–2632). Although this "humanization" process has led to production of monoclonal antibodies that contain 95% human sequences, there remain some sequences of mouse origin. Since therapy with these anti-IgE antibodies requires frequent administration of the antibodies over a long period of time, some treated allergic patients could produce an antibody response against the mouse sequences that still remain within these therapeutic antibodies. The induction of antibodies against the therapeutic anti-IgE would negate the therapeutic impact of these anti-IgE antibodies at least in some patients. Second, the cost of treatment with these antibodies will be very high since high doses of these monoclonal antibodies are required to induce a therapeutic effect. Moreover, the frequency and administration routes with which these antibodies have to be administered are inconvenient. A more attractive strategy for the treatment of IgE-mediated disorders is the administration of peptides which induce the production of anti-IgE antibodies.

One of the most promising treatments for IgE-mediated allergic reactions is the active immunization against appropriate non-anaphylactogenic epitopes on endogenous IgE. Stanworth et al. (U.S. Pat. No. 5,601,821) described a strategy involving the use of a peptide derived from the CH4 domain of the human IgE coupled to a heterologous carrier protein as an allergy vaccine. However, this peptide has been shown not to induce the production of antibodies that react with native soluble IgE. Further, Hellman (U.S. Pat. No. 5,653,980) proposed anti-IgE vaccine compositions based on fusion of full length CH2–CH3 domains (approximately 220 amino acid long) to a foreign carrier protein. However, the antibodies induced by the anti-IgE vaccine compositions proposed in Hellman will most likely result in anaphylaxis since antibodies against some portions of the CH2 and CH3 domains of the IgE molecule have been shown to cross-link the IgE receptor on the surface of mast cell and basophils and lead to production of mediators of anaphylaxis (see, e.g., Stadler et al., 1993, Int. Arch. Allergy and Immunology 102:121–126). Therefore, a need remains for vaccines for the treatment of IgE-mediated allergic reactions which do not induce anaphylactic antibodies.

The significant concern over induction of anaphylaxis has resulted in the development of another approach to the treatment of type I allergic disorders consisting of mimotopes that could induce the production of anti-IgE polyclonal antibodies when administered to animals (see, e.g., Rudolf, et al., 1998, Journal of Immunology 160:3315–3321). Kricek et al. (International Publication No. WO 97/31948) screened phage-displayed peptide libraries with the monoclonal antibody BSW17 to identify peptide mimotopes that could mimic the conformation of the IgE receptor binding. These mimotopes could presumably be used to induce polyclonal antibodies that react with free native IgE, but not with receptor-bound IgE as well as block IgE from binding to its receptor. Kricek et al. disclosed peptide mimotopes that are not homologous to any part of the IgE molecule and are thus different from peptides disclosed in the present invention.

A major obstacle facing the development of an anti-IgE vaccine is the lack of information regarding the precise amino acids representing non-anaphylactogenic IgE determinants that could be safely used to immunize allergic subjects and induce non-anaphylactogenic polyclonal antibodies (i.e., polyclonal anti-IgE antibodies that do not bind to receptor-bound IgE). The peptide compositions of the present invention are selected to be non-anaphylactogenic; i.e., the peptide compositions do not result in production of anti-IgE antibodies that could bind or cause cross-linking of IgE bound to mast cells or basophils. Thus peptides of the present invention have superior safety profile and are differentiated by sequence composition from disclosed vaccines based on full-length C2H–CH3 domains.

SUMMARY OF THE INVENTION

The present invention provides compositions and methods for the use of antigenic peptides derived from the Fc portion of the epsilon heavy chain of IgE molecules as vaccines for the treatment and prevention of IgE-mediated allergic disorders. In one embodiment, the invention provides compositions for the treatment and prevention of IgE-mediated allergic disorders comprising an immunogenic amount of one or more antigenic peptides derived from the CH3 domains of IgE molecules from two unrelated species effective for treatment or prevention of an IgE-mediated allergic disorder. Preferably, compositions of the present invention comprise an immunogenic amount of one or more antigenic peptides comprising the amino acid sequence of SEQ ID NOS: 2, 3, 10, 11, 12, 13 or 14 or an antigenic fragment, derivative or variant thereof.

The antigenic peptides can be supplied by direct administration or indirectly as "pro-drugs" using somatic cell gene therapy.

In a preferred embodiment, the present invention is based, in part, on the discovery that antigenic peptides comprising conserved amino acid residues of the CH3 domain of an IgE molecule from one species flanked by variable amino acid residues of the CH3 domain of an IgE molecule from a second unrelated species are capable of inducing a high titer of anti-IgE antibodies when administered to an animal without causing anaphylaxis. The Applicants compared the primary amino acid sequences of IgE molecules from different species, e.g., rat IgE and dog IgE, and identified conserved amino acid residues in the CH3 domains of the IgE molecules from the different species. The Applicants also determined that the conserved amino acid residues in the CH3 domains of IgE molecules from different species are flanked by amino acid residues that vary from species to species (referred to as "the variable amino acid residues").

Accordingly, in one embodiment, the present invention encompasses antigenic peptides comprising amino acid residues of the CH3 domain of an IgE molecule from a first species flanked by amino acid residues of the CH3 domain of an IgE molecule from a second unrelated species. The amino acid residues of the CH3 domain of the IgE molecule from the first species, which comprise the antigenic peptide, are conserved in the CH3 domain of the IgE molecule of the second unrelated species. However, the amino acid residues of the CH3 domain of the IgE molecule of the second unrelated species which comprise the antigenic peptide are not conserved (i.e., vary) in the CH3 domain of the IgE molecule of the first species. Thus, for example, an antigenic peptide of the present invention could comprise conserved amino acid residues of the CH3 domain of the canine IgE molecule flanked by amino acid residues of the CH3 domain of the rat IgE molecule. Such an antigenic peptide would preferably be administered to a dog to treat or prevent an IgE-mediated allergic disorder. The present invention further provides antigenic fusion proteins derived from a single species, which do not cause anaphylaxis when administered to an animal. Preferably, such an antigenic fusion protein having the sequence SEQ ID NO: 27.

The present invention also provides pharmaceutical compositions comprising an immunogenically effective amount of one or more antigenic peptides derived from the CH3 domains of IgE molecules from the same or from two or more unrelated species and one or more pharmaceutically acceptable carriers. In one embodiment, a pharmaceutical composition of the invention comprises an immunogenically effective amount of one or more antigenic peptides derived from the CH3 domains of IgE molecules from two unrelated species and one or more pharmaceutically acceptable carriers. In another embodiment, a pharmaceutical composition of the invention comprises one or more pharmaceutical carriers and an immunogenically effective amount of one or more antigenic peptide derived from the CH3 domains of IgE molecules from two unrelated species (SEQ ID NOS: 2, 3, and 10–14) and a heterologous carrier protein such as SEQ ID NOS: 9 and 23.

The present invention also provides pharmaceutical compositions comprising an immunogenically effective amount of one or more antigenic peptides derived from the CH3 domains of IgE molecules from two unrelated species, a pharmaceutically acceptable carrier, and an adjuvant. Adjuvants encompass any compound capable of enhancing an immune response to an antigen. Examples of adjuvants which may be effective, include, but are not limited to: aluminum hydroxide, monophosphoryl lipid A (MPLA)-acetyl-muramyl-L-threonyl-D-isoglutamine (thr-MDP), N-acetyl-nor-muramyl-L-alanyl-D-isoglutamine, N-acetylmuramyl-L-alanyl-D-isoglutaminyl-L-alanine-2-(1'-2'-dipalmitoyl-sn-glycero-3-hydroxyphosphoryloxy)-ethylamine, simple immunostimulatory oligonucleotides, cytokines such as IL-12, IL-2 or IL-1, saponins, and microbial toxins such as cholera toxin, heat labile toxin and genetically altered derivatives of them.

In another embodiment, a pharmaceutical composition of the invention comprises a pharmaceutical carrier, an adjuvant and an immunogenically effective amount of one or more antigenic fusion proteins comprising an antigenic peptide derived from the CH3 domains of IgE molecules from two unrelated species and a heterologous carrier protein. In a preferred embodiment, a pharmaceutical composition of the invention comprises a pharmaceutical carrier, an adjuvant and an immunogenically effective amount of one or more antigenic peptides comprising of the amino acid sequence of SEQ ID NOS: 2, 3 and 10–14.

In another preferred embodiment, a pharmaceutical composition of the present invention comprises a pharmaceutical carrier, an adjuvant, and an immunogenically effective amount of one or more fusion proteins comprising the amino acid sequence of SEQ ID NOS: 2, 3, and 10 to 14.

The present invention also provides methods of administering compositions of the invention to animals, preferably mammals and most preferably humans for the treatment or prevention of IgE-mediated allergic disorders. The compositions of the present invention are in suitable formulation to be administered to animals, preferably mammals such as companion animals (e.g., dogs, cats, and horses) and livestock (e.g., cows and pigs), and most preferably humans. The compositions of the invention are administered in an amount effective to elicit an immune response, for example, the production of polyclonal antibodies with specificity for an IgE molecule. In one embodiment, the compositions of the invention are administered in an amount effective to induce the production of polyclonal or monoclonal antibodies with specificity for the Fc portion of an IgE molecule required for IgE to bind to its receptor (i.e., the CH3 domain of an IgE molecule). In a preferred embodiment, the compositions of present invention are administered in an amount effective to induce the production of anti-IgE antibodies which bind to soluble (free) IgE in serum and other bodily fluids, prevent IgE from binding to its high affinity receptors on mast cells and basophils, and do not cross-link receptor-bound IgE. Accordingly, the compositions of the invention are administered in an amount effective to induce the production of polyclonal antibodies which do not induce anaphylaxis for the treatment or prevention of IgE-mediated allergic disorders.

BRIEF DESCRIPTION OF THE FIGURES

FIG. 1. Baculovirus expressed human CH3 domain separated by SDS-SAGE on 4–12% gels under reducing conditions. The 11 kDA CH3 domain can be seen in lane 4. No corresponding bands were observed in the sf-9 cell control (lane 2) or in wild type baculovirus (lane 3). Positions of molecular mass standards (kDa) are indicated in lane 1.

FIG. 2. Immunoblotting of baculovirus expressed Human CH3 domain with rabbit A# 145 RBS-2 antiserum. Samples were separated by SDS-SAGE on 4–12% gels under reducing conditions. The 11 kDA CH3 domain can be seen in lane 4. No bands were observed in the sf-9 cell control (lane 2) or in wild type baculovirus (lane 3). Positions of molecular mass standards (kDa) are indicated in lane 1.

DETAILED DESCRIPTION OF THE INVENTION

The present invention provides compositions and methods for the use of antigenic peptides derived from the Fc portion of the epsilon heavy chain of IgE molecules as vaccines for the treatment and prevention of IgE-mediated allergic disorders. In particular, the present invention provides compositions comprising an immunogenic amount of an antigenic peptide derived from the CH3 domains of IgE molecules from two unrelated species effective for treatment or prevention of an IgE-mediated allergic disorder. Preferably, compositions of the present invention comprise an immunogenic amount of one or more antigenic peptides comprising the amino acid sequence of SEQ ID NOS: 1 to 6 and 10 to 14.

The antigenic peptides of the present invention comprise an amino acid sequence of the CH3 domains of IgE molecules from two unrelated species and induce the production of anti-IgE antibodies, which are not anaphylactic. In particular, the antigenic peptides of the present invention induce the production of anti-IgE antibodies which bind to soluble (free) IgE in serum and other bodily fluids, prevent IgE from binding to its high affinity receptors on mast cells and basophils, and do not cross-link receptor-bound IgE. The antigenic peptides of the present invention may be coupled to one or more heterologous peptides. The antigenic peptides of the invention can be supplied by direct administration or indirectly as "pro-drugs" using somatic cell gene therapy.

In one embodiment, an antigenic peptide of the invention comprises an amino acid sequence comprising amino acid residues of the CH3 domain of an IgE molecule from a first species flanked by amino acid residues of the CH3 domain of an IgE molecule from a second, preferably unrelated, species. An antigenic peptide of the invention comprises at least 10 amino acid residues of the CH3 domain of an IgE molecule from a first species, at least 15 amino acid residues of the CH3 domain of an IgE molecule from a first species, at least 20 amino acid residues of the CH3 domain of an IgE molecule from a first species, or at least 25 amino acid residues of the CH3 domain of an IgE molecule from a first species. Further, an antigenic peptide of the invention comprises at least 10 amino acid residues of the CH3 domain of an IgE molecule from a second species, at least 15 amino acid residues of the CH3 domain of an IgE molecule from a second species, at least 20 amino acid residues of the CH3 domain of an IgE molecule from a second species, or at least 25 amino acid residues of the CH3 domain of an IgE molecule from a second species.

In specific embodiments, an antigenic peptide of the invention is at least 10 amino acid residues long, at least 15 amino acid residues long, at least 20 amino acid residues long, or at least 25 amino acid residue long, or at least 30 amino acid residues long. In a preferred embodiment, an antigenic peptide of the invention comprises an amino acid sequence comprising amino acid residues of the CH3 domain of an IgE molecule from a first species flanked by amino acid residues of the CH3 domain of an IgE molecule from a second unrelated species and said antigenic peptide is between 28 and 31 amino acid residues. The present invention also provides antigenic fusion proteins comprising an antigenic peptide and a heterologous carrier protein. In a specific embodiment, an antigenic fusion protein comprises amino acid residues of the CH3 domain of an IgE molecule from a first species flanked by amino acid residues of the CH3 domain of an IgE molecule from a second unrelated species and a heterologous protein carrier. In a preferred embodiment, an antigenic fusion protein of the present invention comprises the amino acid sequence of SEQ ID NOS: 2, 3, and 10 to 14.

The present invention also provides antigenic peptides or antigenic fusion proteins of the invention in which one or more amino acid substitutions, additions or deletions has been introduced. Mutations can be introduced by standard techniques known to those of skill in the art. For example, one or more mutations at the nucleotide level which result in one or more amino acid mutations can be introduced by site-directed mutagenesis or PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for their ability to induce anti-IgE antibodies which do not cause anaphylaxis.

The present invention also provides methods for treating or preventing IgE-mediated allergic disorders in animals, preferably mammals and most preferably humans, comprising administering pharmaceutical compositions, which do not induce anaphylaxis. The pharmaceutical compositions to be administered in accordance with the methods of the present invention encompass antigenic peptides derived from the CH3 domains of IgE molecules from two unrelated species. The pharmaceutical compositions to be administered in accordance with the methods of the present invention also include: (i) recombinant antigenic peptides having an amino acid sequence comprising amino acid residues of the CH3 domain of an IgE molecule from a first species flanked by amino acid residues of the CH3 domain of an IgE molecule from a second species; (ii) recombinant antigenic fusion proteins comprising amino acid residues of the CH3 domain of an IgE molecule from a first species flanked by amino acid residues of the CH3 domain of an IgE molecule from a second species and a heterologous carrier protein; (iii) plasmid compositions comprising polynucleotide encoding an antigenic peptide having an amino acid sequence comprising amino acid residues of the CH3 domain of an IgE molecule from a first species flanked by amino acid residues of the CH3 domain of an IgE molecule from a second species; and (iv) plasmid compositions comprising polynucleotides encoding for antigenic fusion proteins comprising amino acid residues of the CH3 domain of an IgE molecule from a first species flanked by amino acid residues of the CH3 domain of an IgE molecule from a second species and a heterologous carrier protein.

In one embodiment, a pharmaceutical composition of the present invention comprises one or more antigenic peptides having the amino acid sequence comprising amino acid residues of the CH3 domain of an IgE molecule from a first species flanked by amino acid residues of the CH3 domain of an IgE molecule from a second species. In a preferred embodiment, a pharmaceutical composition of the present invention comprises one or more antigenic peptides between 28 and 31 amino acid residues long having the amino acid sequence comprising amino acid residues of the CH3 domain of an IgE molecule from a first species flanked by amino acid residues of the CH3 domain of an IgE molecule from a second unrelated species. In accordance with these embodiments, the pharmaceutical compositions may further comprise an adjuvant.

The present invention also provides pharmaceutical compositions comprising one or more antigenic fusion proteins. In a specific embodiment, a pharmaceutical composition of the present invention comprises one or more antigenic fusion proteins comprising an antigenic peptide of the invention and a heterologous carrier protein. In accordance with this embodiment, the pharmaceutical composition may further comprise an adjuvant.

As used herein the term "heterologous carrier protein" refers to a protein which does not possess high homology to a protein found in the species that is receiving a composition of the invention and elicits an immune response. A protein possesses high homology if it is greater than at least 75% identical, more preferably at least 85% identical or at least 90% identical to a protein as determined by any known mathematical algorithm utilized for the comparison of two amino acid sequences (see, e.g., Karlin and Altschul, 1990, Proc. Natl. Acad. Sci. USA 87: 2264–2268; Karlin and Altschul, 1993, Proc. Natl. Acad. Sci. USA 90: 5873–5877; Torellis and Robotti, 1994, Comput. Appl. Biosci. 10: 3–5; and Pearson and Lipman, 1988, Proc. Natl. Acad. Sci. 85: 2444–8). Preferably, the percent identity of two amino acid sequences is determined by BLAST protein searches with the XBLAST program, score=50, wordlength=3. Examples of heterologous carrier proteins include, but are not limited to, SEQ ID NOS: 7, 8 or 9, KLH, PhoE, and rmLT.

A heterologous carrier protein can be fused to the N-terminus, C-terminus or both termini of an antigenic peptide of the invention. Antigenic fusion proteins of the invention can be produced by techniques known to those of skill in the art, for example, by standard recombinant DNA techniques. For example, a nucleotide sequence encoding an antigenic fusion protein can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a gene sequence encoding an antigenic fusion protein (see, e.g., Ausubel et al., infra). Moreover, many expression vectors are commercially available that already encode a fusion moiety (e.g., a GST polypeptide). A nucleic acid encoding an antigenic peptide of the invention can be cloned into such an expression vector such that the fusion moiety is linked in-frame to the antigenic peptide of the invention.

In a specific embodiment, a pharmaceutical composition of the present invention comprises an antigenic peptide having an amino acid sequence comprising amino acid residues of SEQ ID NOS 2, 3 and 10 to 14.

In another embodiment, a pharmaceutical composition of the present invention comprises an antigenic fusion protein comprising the amino acid sequence of SEQ ID NOS: 2, 3 and 10 to 14. In accordance with these embodiments, the pharmaceutical compositions may further comprise an adjuvant.

The pharmaceutical compositions of the present invention are in suitable formulation to be administered to animals such as companion animals (e.g., dogs and cats) and livestock (e.g., pigs, cows and horses) and humans for the treatment or prevention of IgE-mediated allergic disorders.

IgE mediated disorders include allergic rhinitis/hay fever, asthma, atopic dermatitis, flea allergy, food allergy and inhalant allergy.

Preferably, a pharmaceutical composition of the invention comprising an antigenic peptide of the invention is administered to the same species as the amino acid residues derived from the CH3 domain of an IgE molecule of the first species to treat or prevent an IgE-mediated allergic disorder. IgE-mediated allergic disorders include, but are not limited to, asthma, allergic rhinitis, gastrointestinal allergies such as food allergies, eosinophilia, and conjunctivitis. The pharmaceutical compositions of the invention are administered to a subject (an animal) in an amount effective for the treatment, prevention or inhibition of IgE-mediated allergic disorders, or an amount effective for inducing an anti-IgE response that is not anaphylactic, or an amount effective for inhibiting or reducing the release of vasoactive substances such as histamine, or an amount effective for alleviating one or more symptoms associated with an IgE-mediated allergic disorder.

The pharmaceutical compositions of the invention can be used with any known method of treating IgE-mediated allergic disorders. In one embodiment, one or more pharmaceutical compositions of the invention and one or more antihistamines are administered to an animal for the treatment or prevention of an IgE-mediated allergic disorder. In another embodiment, one or more pharmaceutical compositions of the invention and one or more corticosteroids are administered to an animal for the treatment or prevention of an IgE-mediated allergic disorder. In yet another embodiment, one or more pharmaceutical compositions of the invention and one or more anti-IgE monoclonal antibodies (e.g., BSW17) are administered to an animal for the treatment or prevention of an IgE-mediated allergic disorder.

The present invention encompasses polynucleotide sequences encoding the antigenic peptides (SEQ ID NOS: 2, 3 and 10 to 14), carrier proteins (SEQ ID NOS: 7, 8 and 9) or antigenic fusion proteins (SEQ ID NOS: 2, 3, and 10 to 14) of the invention. The present invention provides nucleic acid molecules comprising different polynucleotide sequences due to the degeneracy of the genetic code which encode identical antigenic peptides and antigenic fusion proteins. The polynucleotide sequence of a CH3 domain of an IgE molecule can be obtained from scientific literature, Genbank, or using cloning techniques known to those of skill in the art. In particular, the present invention encompasses polynucleotide sequences encoding human, rat and canine CH3 domain of an IgE molecule disclosed in Genbank Accession Numbers S53497, X00923, and L36872; respectively, are incorporated herein by reference.

The present invention also encompasses antigenic fusion proteins comprising an antigenic peptide of the invention encoded by a polynucleotide sequence from two different species and a heterologous carrier protein encoded by a polynucleotide sequence of a different species from the antigenic peptide. The polynucleotide sequence of a heterologous carrier protein can be obtained from scientific literature, Genbank, or using cloning techniques known to those of skill in the art.

The polynucleotide sequence encoding an antigenic peptide or an antigenic fusion protein of the invention can be inserted into an appropriate expression vector, i.e., a vector, which contains the necessary elements for the transcription and translation of the inserted protein-coding sequence. The necessary transcriptional and translational signals can also be supplied by the native IgE genes or its flanking regions. A variety of host-vector systems may be utilized to express the protein-coding sequence. These include but are not limited to mammalian cell systems infected with virus (e.g., vaccinia virus, adenovirus, etc.); insect cell systems infected with virus (e.g., baculovirus); microorganisms such as yeast containing yeast vectors, or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used.

Any of the methods previously described for the insertion of DNA fragments into a vector may be used to construct expression vectors containing polynucleotides encoding antigenic peptides or antigenic fusion proteins, and appropriate transcriptional and translational control signals. These methods may include in vitro recombinant DNA and synthetic techniques and in vivo recombinants (genetic recombination). Expression of the nucleic acid sequence encoding an antigenic peptide or an antigenic fusion protein of the invention may be regulated by a second nucleic acid sequence so that the antigenic peptide or the antigenic fusion protein is expressed in a host transformed with the recombinant DNA molecule. For example, expression of an antigenic peptide or an antigenic fusion protein of the invention may be controlled by any promoter or enhancer element known in the art. Promoters which may be used to control the expression of an antigenic peptide or an antigenic fusion protein of the invention include, but are not limited to, the Cytomeglovirus (CMV) immediate early promoter region, the SV40 early promoter region (Bernoist and Chambon, 1981, Nature 290: 304–310), the promoter contained in the 3' long terminal repeat of Rous sarcoma virus (Yamamoto, et al., 1980, Cell 22: 787–797), the herpes thymidine kinase promoter (Wagner et al., 1981, Proc. Natl. Acad. Sci. USA 78: 1441–1445), the regulatory sequences of the metallothionein gene (Brinster et al., 1982, Nature 296: 39–42); prokaryotic expression vectors such as the β-lactamase promoter (Villa-Kamaroff et al., 1978, Proc. Natl. Acad. Sci. USA 75: 3727–3731), or the tac promoter (DeBoer et al., 1983, Proc. Natl. Acad. Sci. USA 80: 21–25); see also "Useful proteins from recombinant bacteria" in Scientific American, 1980, 242: 74–94; plant expression vectors comprising the nopaline synthetase promoter region (Herrera-Estrella et al., Nature 303: 209–213) or the cauliflower mosaic virus 35S RNA promoter (Gardner et al., 1981, Nucl. Acids Res. 9: 2871), and the promoter of the photosynthetic enzyme ribulose biphosphate carboxylase (Herrera-Estrella et al., 1984, Nature 310: 115–120); promoter elements from yeast or other fungi such as the Gal 4 promoter, the ADC (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase I gene control region which is active in pancreatic acinar cells (Swift et al., 1984, Cell 38: 639–646; Ornitz et al., 1986, Cold Spring Harbor Symp. Quant. Biol. 50: 399–409; MacDonald, 1987, Hepatology 7:425–515); insulin gene control region which is active in pancreatic beta cells (Hanahan, 1985, Nature 315: 115–122); immunoglobulin gene control region which is active in lymphoid cells (Grosschedl et al., 1984, Cell 38: 647–658; Adames et al., 1985, Nature 318: 533–538; and Alexander et al., 1987, Mol. Cell. Biol. 7: 1436–1444); mouse mammary tumor virus control region which is active in testicular, breast, lymphoid and mast cells (Leder et al., 1986, Cell 45: 485–495); albumin gene control region which is active in liver (Pinkert et al., 1987, Genes and Devel. 1: 268–276); alpha-fetoprotein gene control region which is active in liver (Krumlauf et al., 1985, Mol. Cell. Biol. 5: 1639–1648; and Hammer et al., 1987, Science 235: 53–58); alpha 1-antitrypsin gene control region which is active in the liver (Kelsey et al., 1987, Genes and Devel. 1: 161–171); beta-globin gene control region which is active in myeloid cells (Mogram et al., 1985, Nature 315: 338–340; and Kollias et al., 1986, Cell 46: 89–94); myelin basic protein gene control region which is active in oligodendrocyte cells in the brain (Readhead et al., 1987, Cell 48: 703–712); myosin light chain-2 gene control region which is active in skeletal muscle (Sani, 1985, Nature 314: 283–286); swine alpha-skeletal actin control region which is active in muscle (Reecy, M. et al., 1998, Animal Biotechnology 9: 101–120) ;and gonadotropic releasing hormone gene control region which is active in the hypothalamus (Mason et al., 1986, Science 234: 1372–1378).

In a specific embodiment, a vector is used that comprises a promoter operably linked to an antigenic peptide-encoding nucleic acid, one or more origins of replication, and, optionally, one or more selectable markers (e.g., an antibiotic resistance gene). In another specific embodiment, a vector is used that comprises a promoter operably linked to an antigenic fusion protein-encoding nucleic acid, one or more origins of replication, and, optionally, one or more selectable markers (e.g., an antibiotic resistance gene).

Expression vectors containing gene inserts can be identified by three general approaches: (a) nucleic acid hybridization; (b) presence or absence of "marker" gene functions; and (c) expression of inserted sequences. In the first approach, the presence of antigenic peptide-encoding polynucleotides or antigenic fusion protein-encoding polynucleotides inserted in an expression vector(s) can be detected by nucleic acid hybridization using probes comprising sequences that are homologous to the inserted polynucleotide sequence. In the second approach, the recombinant vector/host system can be identified and selected based upon the presence or absence of certain "marker" gene functions (e.g., thymidine kinase activity, resistance to antibiotics, transformation phenotype, occlusion body formation in baculovirus, etc.) caused by the insertion of the gene(s) in the vector(s). For example, if a nucleic acid molecule encoding an antigenic peptide or an antigenic fusion protein is inserted within the marker gene sequence of the vector, recombinants containing the nucleic acid molecule encoding the antigenic peptide or the antigenic fusion protein insert can be identified by the absence of the marker gene function. In the third approach, recombinant expression vectors can be identified by assaying the gene product expressed by the recombinant. Such assays can be based, for example, on the physical or functional properties of an antigenic peptide or an antigenic fusion protein in in vitro assay systems, e.g., binding of an antigenic peptide or an antigenic fusion protein with an anti-IgE antibody.

Once a particular recombinant DNA molecule is identified and isolated, several methods known in the art may be used to propagate it. Once a suitable host system and growth conditions are established, recombinant expression vectors can be propagated and prepared in quantity. As previously explained, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

The term "host cell" as used herein refers not only to the particular subject cell into which a recombinant DNA molecule is introduced but also to the progeny or potential progeny of such a cell. Because certain modifications may occur in succeeding generations due to either mutation or environmental influences, such progeny may not, in fact, be identical to the parent cell, but are still included within the scope of the term as used herein.

A host cell strain may be chosen which modulates the expression of the inserted sequences, or modifies and processes the gene product in the specific fashion desired. Expression from certain promoters can be elevated in the presence of certain inducers; thus, expression of the genetically engineered may be controlled. Furthermore, different host cells have characteristic and specific mechanisms for the translational and post-translational processing and modification (e.g., glycosylation, phosphorylation of proteins). Appropriate cell lines or host systems can be chosen to ensure the desired modification and processing of the foreign protein expressed. For example, expression in a bacterial system can be used to produce an unglycosylated core protein product. Expression in yeast will produce a glycosylated product. Expression in mammalian cells can be used to ensure "native" glycosylation of an antigenic peptide or antigenic fusion protein of the invention. Furthermore, different vector/host expression systems may effect processing reactions to different extents.

For long-term, high-yield production of recombinant proteins, stable expression is preferred. For example, cell lines which stably express an antigenic peptide or an antigenic fusion protein of the invention may be engineered.

Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express an antigenic peptide or an antigenic protein of the invention. Such engineered cell lines may be particularly useful in the screening and evaluation of anti-IgE antibodies or other agents (e.g., organic molecules, inorganic molecules, organic/inorganic complexes, polypeptides, peptides, peptide mimics, polysaccharides, saccharides, glycoproteins, nucleic acids, DNA and RNA strands and oligonucleotides, etc.) that affect binding of an IgE molecule to its receptor.

A number of selection systems may be used, including but not limited to the herpes simplex virus thymidine kinase (Wigler et al., 1977, Cell 11: 223), hypoxanthine-guanine phosphoribosyltransferase (Szybalska & Szybalski, 1962, Proc. Natl. Acad. Sci. USA 48: 2026), and adenine phosphoribosyltransferase (Lowy et al., 1980, Cell 22: 817) genes can be employed in tk$^-$, hgprt$^-$ or aprt$^-$ cells, respectively. Also, antimetabolite resistance can be used as the basis of selection for dhfr, which confers resistance to methotrexate (Wigler et al., 1980, Proc. Natl. Acad. Sci. USA 77: 3567; O'Hare et al., 1981, Proc. Natl. Acad. Sci. USA 78: 1527); gpt, which confers resistance to mycophenolic acid (Mulligan & Berg, 1981, Proc. Natl. Acad. Sci. USA 78: 2072); neo, which confers resistance to the aminoglycoside G-418 (Colberre-Garapin et al., 1981, J. Mol. Biol. 150: 1); and hygro, which confers resistance to hygromycin (Santerre et al., 1984, Gene 30: 147) genes.

In a specific embodiment, one or more nucleic acid molecules comprising a polynucleotide sequence encoding an antigenic peptide of the invention, are administered to treat or prevent IgE-mediated allergic disorders, by way of gene therapy. In another specific embodiment, one or more nucleic acid molecules comprising a polynucleotide sequence encoding an antigenic fusion protein, are administered to treat or prevent IgE-mediated allergic disorders, by way of gene therapy. In yet another specific embodiment, one or more nucleic acid molecules comprising a polynucleotide sequence encoding an antigenic peptide of the invention, and one or more nucleic acid molecules comprising a polynucleotide sequence encoding an antigenic fusion protein of the invention are administered to treat or prevent IgE-mediated allergic disorders, by way of gene therapy. Gene therapy refers to therapy performed by the administration to a subject of an expressed or expressible nucleic acid. In this embodiment of the invention, the nucleic acids produce their encoded antigenic peptides or antigenic fusion proteins that mediate a therapeutic effect by eliciting an immune response such as the production of anti-IgE antibodies.

Any of the methods for gene therapy available in the art can be used according to the present invention. Exemplary methods are described below.

For general reviews of the methods of gene therapy, see Goldspiel et al., 1993, Clinical Pharmacy 12: 488–505; Wu and Wu, 1991, Biotherapy 3: 87–95; Tolstoshev, 1993, Ann. Rev. Pharmacol. Toxicol. 32: 573–596; Mulligan, 1993, Science 260: 926–932; and Morgan and Anderson, 1993, Ann. Rev. Biochem. 62: 191–217; May, 1993, TIBTECH 11(5):155–215). Methods commonly known in the art of recombinant DNA technology which can be used are described in Ausubel et al. (eds.), 1993, Current Protocols in Molecular Biology, John Wiley & Sons, NY; and Kriegler, 1990, Gene Transfer and Expression, A Laboratory Manual, Stockton Press, NY.

In a preferred aspect, a pharmaceutical composition comprises nucleic acid sequences encoding an antigenic peptide of the invention, said nucleic acid sequences being part of expression vectors that express the antigenic peptide in a suitable host. In particular, such nucleic acid sequences have promoters operably linked to the antigenic peptide coding regions, said promoters being inducible or constitutive, and, optionally, tissue-specific. In another preferred aspect, a pharmaceutical composition comprises nucleic acid sequences encoding an antigenic fusion protein of the invention, said nucleic acid sequences being part of expression vectors that express the antigenic fusion protein in a suitable host. In particular, such nucleic acid sequences have promoters operably linked to the antigenic fusion protein coding regions, said promoters being inducible or constitutive, and, optionally, tissue-specific. In another particular embodiment, nucleic acid molecules are used in which the coding sequences of an antigenic peptide of the invention and any other desired sequences are flanked by regions that promote homologous recombination at a desired site in the genome, thus providing for intrachromosomal expression of the nucleic acids encoding the antigenic peptide (Koller and Smithies, 1989, Proc. Natl. Acad. Sci. USA 86:8932–8935; and Zijlstra et al., 1989, Nature 342:435–438). In another particular embodiment, nucleic acid molecules are used in which the coding sequences of an antigenic fusion protein of the invention and any other desired sequences are flanked by regions that promote homologous recombination at a desired site in the genome, thus providing for intrachromosomal expression of the nucleic acids encoding the antigenic protein.

Delivery of the nucleic acids into a patient may be either direct, in which case the patient is directly exposed to the nucleic acid or nucleic acid-carrying vectors, or indirect, in which case, cells are first transformed with the nucleic acids in vitro, then transplanted into the patient. These two approaches are known, respectively, as in vivo or ex vivo gene therapy.

In a specific embodiment, the nucleic acid sequences are directly administered in vivo, where it is expressed to produce the encoded product. This can be accomplished by any of numerous methods known in the art, e.g., by constructing them as part of an appropriate nucleic acid expression vector and administering it so that they become intracellular, e.g., by infection using defective or attenuated retrovirals or other viral vectors (see U.S. Pat. No. 4,980, 286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, 1987, J. Biol. Chem. 262: 4429–4432) (which can be used to target cell types specifically expressing the receptors), etc. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180 dated Apr. 16, 1992 (Wu et al.); WO 92/22635 dated Dec. 23, 1992 (Wilson et al.); WO92/20316 dated Nov. 26, 1992 (Findeis et al.); WO93/14188 dated Jul. 22, 1993 (Clarke et al.); and WO 93/20221 dated Oct. 14, 1993 (Young)). Alternatively, the nucleic acid can be introduced intracellularly and incorporated within host cell DNA for expression, by homologous recombination (Koller and Smithies, 1989, Proc. Natl. Acad. Sci. USA 86: 8932–8935; Zijlstra et al., 1989, Nature 342: 435–438).

In specific embodiments, viral vectors that contain nucleic acid sequences encoding antigenic peptides or antigenic fusion proteins are used. For example, a retroviral vector containing nucleic acid sequences encoding an antigenic peptide or an antigenic fusion protein can be used (see, e.g., Miller et al., 1993, Meth. Enzymol. 217: 581–599). These retroviral vectors have been to delete retroviral sequences that are not necessary for packaging of the viral genome and integration into host cell DNA. The nucleic acid sequences encoding antigenic peptides or antigenic fusion proteins to be used in gene therapy are cloned into one or more vectors, which facilitates delivery of the gene into a patient. More detail about retroviral vectors can be found in Boesen et al., 1994, Biotherapy 6: 291–302, which describes the use of a retroviral vector to deliver the mdr1 gene to hematopoietic stem cells in order to make the stem cells more resistant to chemotherapy. Other references illustrating the use of retroviral vectors in gene therapy are: Clowes et al., 1994, J. Clin. Invest. 93: 644–651; Kiem et al., 1994, Blood 83: 1467–1473; Salmons and Gunzberg, 1993, Human Gene Therapy 4: 129–141; and Grossman and Wilson, 1993, Curr. Opin. in Genetics and Devel. 3:110–114.

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, 1993, Current Opinion in Genetics and Development 3: 499–503 present a review of adenovirus-based gene therapy. Bout et al., 1994, Human Gene Therapy 5: 3–10 demonstrated the use of adenovirus vectors to transfer genes to the respiratory epithelia of rhesus monkeys. Other instances of the use of adenoviruses in gene therapy can be found in Rosenfeld et al., 1991, Science 252: 431–434; Rosenfeld et al., 1992, Cell 68: 143–155; Mastrangeli et al., 1993, J. Clin. Invest. 91: 225–234; PCT Publication WO94/12649; and Wang, et al., 1995, Gene Therapy 2: 775–783. In a preferred embodiment, adenovirus vectors are used. Adeno-associated virus (AAV) has also been proposed for use in gene therapy (see, e.g, Walsh et al., 1993, Proc. Soc. Exp. Biol. Med. 204: 289–300; and U.S. Pat. No. 5,436,146).

Another approach to gene therapy involves transferring a nucleic acid molecule to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid molecule is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign nucleic acid molecules into cells (see, e.g., Loeffler and Behr, 1993, Meth. Enzymol. 217: 599–618; Cohen et al., 1993, Meth. Enzymol. 217: 618–644; Cline, 1985, Pharmac. Ther. 29: 69–92) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a subject by various methods known in the art. Recombinant blood cells (e.g., hematopoietic stem or progenitor cells) are preferably administered intravenously. The amount of cells envisioned for use depends on the desired effect, subject's state, etc., and can be determined by one skilled in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as T lymphocytes, B lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

In a preferred embodiment, the cell used for gene therapy is autologous to the subject.

In an embodiment in which recombinant cells are used in gene therapy, nucleic acid sequences encoding the antigenic peptides or antigenic fusion proteins of the invention are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention (see e.g., PCT Publication WO 94/08598, dated Apr. 28, 1994; Stemple and Anderson, 1992, Cell 71: 973–985; Rheinwald, 1980, Meth. Cell Bio. 21A: 229; and Pittelkow and Scott, 1986, Mayo Clinic Proc. 61: 771).

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription.

The invention also relates to methods for producing an antigenic peptide of the invention or an antigenic fusion protein of the invention comprising growing a culture of the cells of the invention in a suitable culture medium, and purifying the protein from the culture. For example, the methods of the invention include a process for producing an antigenic peptide or an antigenic fusion protein of the invention in which a host cell (i.e., a prokaryotic or eukaryotic cell) containing a suitable expression vector that includes a polynucleotide encoding an antigenic peptide or an antigenic fusion protein is cultured under conditions that allow expression of the encoded antigenic peptide or the encoded antigenic fusion protein. The antigenic peptide or the antigenic fusion protein can be recovered from the culture, conveniently from the culture medium, and further purified. The purified antigenic peptides or antigenic fusion proteins can be used in in vitro immunoassays which are well known in the art to identify anti-IgE antibodies which bind to the antigenic peptides or the antigenic fusion proteins.

The protein may also be produced by operably linking the isolated polynucleotide of the invention to suitable control sequences in one or more insect expression vectors, and employing an insect expression system. Materials and methods for baculovirus/insect cell expression systems are commercially available in kit form from, e.g., Invitrogen, San Diego, Calif., U.S.A. (the MaxBat.RTM. kit), and such methods are well known in the art, as described in Summers and Smith, Texas Agricultural Experiment Station Bulletin No. 1555 (1987), incorporated herein by reference. As used herein, an insect cell capable of expressing a polynucleotide of the present invention is "transformed."

Alternatively, an antigenic peptide of the invention or an antigenic fusion protein of the invention may also be expressed in a form which will facilitate purification. For example, an antigenic peptide may be expressed as fusion protein comprising a heterologous protein such as maltose binding protein (MBP) glutathione-S-transferase (GST) or thioredoxin (TRX) which facilitate purification. Kits for expression and purification of such fusion proteins are commercially available from New England BioLab (Beverly, Mass.), Pharmacia (Piscataway, N.J.) and In Vitrogen, respectively. The protein can also be tagged with an epitope and subsequently purified by using a specific antibody directed to such epitope. One such epitope ("Flag") is commercially available from Kodak (New Haven, Conn.).

The antigenic peptides of the invention or the antigenic fusion proteins of the invention may also be expressed as a product of transgenic animals, e.g., as a component of the milk of transgenic cows, goats, pigs, or sheep which are characterized by somatic or germ cells containing a nucleotide sequence encoding the antigenic peptide or the antigenic fusion protein.

Any method known to those of skill in the art can be used to produce an antigenic peptide or an antigenic fusion protein of the invention. At the simplest level, the amino acid sequence can be synthesized using commercially available peptide synthesizers. This is particularly useful in producing small peptides and fragments of larger polypeptides. The isolated antigenic peptides and antigenic fusion proteins of the invention are useful, for example, in generating antibodies against the native polypeptide.

One skilled in the art can readily follow known methods for isolating peptides and proteins in order to obtain one of the isolated antigenic peptides or antigenic fusion proteins of the present invention. These include, but are not limited to, immunochromatography, high performance liquid chromatography (HPLC), reverse-phase high performance liquid chromatography (RP-HPLC), size-exclusion chromatography, ion-exchange chromatography, and immuno-affinity chromatography. See, e.g., Scopes, Protein Purification: Principles and Practice, Springer-Verlag (1994); Sambrook et al., in Molecular Cloning: A Laboratory Manual; Ausubel et al., Current Protocols in Molecular Biology.

An antigenic peptide or an antigenic fusion protein of the invention is "isolated" or "purified" when it is substantially free of cellular material or other contaminating proteins from the cell or tissue source from which the protein is derived, or substantially free of chemical precursors or other chemicals when chemically synthesized. The language "substantially free of cellular material" includes preparations of protein in which the protein is separated from cellular components of the cells from which it is isolated or recombinantly produced. Thus, protein that is substantially free of cellular material includes preparations of protein having less than about 30%, 20%, 10%, or 5% (by dry weight) of a contaminating protein. When an antigenic peptide or an antigenic fusion protein of the invention is recombinantly produced, it is also preferably substantially free of culture medium, i.e., culture medium represents less than about 20%, 10%, or 5% of the volume of the protein preparation. When an antigenic peptide or an antigenic fusion protein of the invention is produced by chemical synthesis, it is preferably substantially free of chemical precursors or other chemicals, i.e., it is separated from chemical precursors or other chemicals which are involved in the synthesis of the antigenic peptide or the antigenic fusion protein. Accordingly such preparations of the protein have less than about 30%, 20%, 10%, 5% (by dry weight) of chemical precursors or compounds other than the antigenic peptide or the antigenic fusion protein.

The compositions of the invention are preferably tested in vitro, and then in vivo for the desired therapeutic or prophylactic activity, prior to use in humans. For example, in vitro assays which can be used to determine whether administration of a specific composition is indicated, include in vitro cell culture assays in which a patient tissue sample is grown in culture, and exposed to or otherwise administered a composition, and the effect of such composition upon the tissue sample is observed.

The expression of an antigenic peptide or an antigenic fusion protein can be assayed by the immunoassays, gel electrophoresis followed by visualization, or any other method known to those skilled in the art.

In various specific embodiments, in vitro assays can be carried out with representative cells of cell types involved in a patient's disorder, to determine if a composition has a desired effect upon such cell types. In accordance with the present invention, the functional activity of an antigenic peptide or an antigenic fusion protein can be measured by its ability to induce anti-IgE antibodies that inhibit IgE from binding to its receptor on mast cells or basophils in vitro without inducing the release of vasoactive substances such as histamine.

Compositions for use in therapy can be tested in suitable animal model systems prior to testing in humans, including but not limited to pigs, chicken, cows or monkeys.

The invention provides methods of treatment (and prophylaxis) by administration to a subject of an effective amount of a composition of the invention to elicit the production of anti-IgE antibodies which do not cause anaphylaxis. In a preferred aspect, a composition of the invention is substantially purified (e.g., substantially free from substances that limit its effect or produce undesired side-effects). The subject is preferably an animal, including but not limited to animals such as cows, pigs, horses, chickens, cats, dogs, etc., and is preferably a mammal, and most preferably human.

Formulations and methods of administration that can be employed when the composition comprises a nucleic acid are described above; additional appropriate formulations and routes of administration can be selected from among those described herein below.

Various delivery systems are known and can be used to administer a composition of the invention, e.g., encapsulation in liposomes, microparticles, microcapsules, recombinant cells capable of expressing the composition, receptor-mediated endocytosis (see, e.g., Wu and Wu, 1987, J. Biol. Chem. 262: 4429–4432), construction of a nucleic acid as part of a retroviral or other vector, etc. Methods of introduction include but are not limited to intratumoral, intradermal, intramuscular, intraperitoneal, intravenous, subcutaneous, intranasal, epidural, and oral routes. The compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, pulmonary administration can be employed, e.g., by use of an inhaler or nebulizer, and formulation with an aerosolizing agent.

In a specific embodiment, it may be desirable to administer the pharmaceutical compositions of the invention locally to the area in need of treatment; this may be achieved by, for example, and not by way of limitation, local infusion, topical application, injection, or by means of an implant, said implant being of a porous, non-porous, or gelatinous material, including membranes, such as sialastic membranes, or fibers. In one embodiment, administration can be by direct injection at the site (or former site) of an allergic reaction.

In another embodiment, a composition of the invention can be delivered in a vesicle, in particular a liposome (see, e.g., Langer, 1990, Science 249: 1527–1533; Treat et al., in Liposomes in the Therapy of Infectious Disease and Cancer, Lopez-Berestein and Fidler (eds.), Liss, New York, pp. 353–365 (1989); and Lopez-Berestein, ibid., pp. 317–327; see generally ibid.)

In yet another embodiment, a composition of the invention can be delivered in a controlled release system. In one embodiment, a pump may be used (see, e.g., Langer, supra; Sefton, 1987, CRC Crit. Ref. Biomed. Eng. 14: 201; Buchwald et al., 1980, Surgery 88: 507; and Saudek et al., 1989, N. Engl. J. Med. 321: 574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, 1983, J. Macromol. Sci. Rev. Macromol. Chem. 23: 61; see also Levy et al., 1985, Science 228: 190; During et al., 1989, Ann. Neurol. 25: 351; and Howard et al.,1989, J. Neurosurg. 71: 105). In yet another embodiment, a controlled release system can be placed in proximity of the therapeutic target, thus requiring only a fraction of the systemic dose (see, e.g., Goodson, in Medical Applications of Controlled Release, supra, vol. 2, pp. 115–138 (1984)).

Other controlled release systems are discussed in the review by Langer (1990, *Science* 249: 1527–1533).

In a specific embodiment where the composition of the invention is a nucleic acid encoding an antigenic peptide or an antigenic fusion protein of the invention, the nucleic acid can be administered in vivo to promote expression of its encoded antigenic peptide or antigenic fusion protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., 1991, Proc. Natl. Acad. Sci. USA 88: 1864–1868), etc. Alternatively, a nucleic acid can be introduced intracellularly and incorporated within host cell DNA for expression, by homologous recombination.

The present invention also provides pharmaceutical compositions. Such compositions comprise a therapeutically effective amount of an antigenic peptide or an antigenic fusion protein of the invention, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the antigenic peptide or the antigenic fusion protein, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The antigenic peptides or antigenic fusion proteins of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The following examples further illustrate the invention.

EXAMPLES

1. Selection of Antigenic Peptides and Cloning of Corresponding Polyneucleotide Sequences A major obstacle facing the development of an anti-IgE vaccine is the lack of information regarding the precise amino acids representing non-anaphylactogenic IgE determinants that could be safely used to immunize allergic subjects and induce non-anaphylactogenic polyclonal antibodies (i.e. polyclonal anti-IgE antibodies that do not bind to receptor-bound IgE). By definition, those determinants ideally correspond to only those IgE amino acid sequences that physically contact the IgE receptor. Clearly, there is no information in the prior art on the precise identity of those sequences. Indeed, the prior art is inconsistent on even the region or domain of IgE within which those sequences may reside. Furthermore, the identity of non-anaphylactogenic determinants could be correctly elucidated from only solving the crystal structure of IgE-IgE receptor complex which, unfortunately, has not yet been achieved. Consequently, the present invention overcome this obstacle and provide IgE determinants capable of inducing within allergic hosts therapeutically desirable polyclonal antibodies that react with native serum IgE, prevent IgE from binding to its receptor on mast cells and basophils and do not react with receptor-bound IgE. In order to identify non-anaphylactogenic IgE epitopes suitable for inclusion into an anti-IgE vaccine, we follow an approach that does not make any a priori assumptions about the location or require knowledge of the exact amino acids on IgE suitable for an effective and safe vaccine. The IgE antibody has been to shown to exist in many species throughout the animal kingdom including for example humans, dogs, cats, sheep, cows, pigs, horses, rats, mice and chimpanzee. Indeed the IgE gene and its encoded protein have been identified in all these species. Comparison of the primary amino acid sequence among these IgE molecules shows that they share common amino acid sequences in many locations throughout the IgE molecule. These common (conserved) sequences are flanked by amino acid sequences that vary among the various IgE molecules. We reasoned that a comparison of the primary sequence of IgE molecules from different species e.g. rat IgE and dog IgE would provide clues to identification of non-anaphylactogenic IgE determinants. It is known that dog, cat, and rat IgE bind to the human IgE receptor. Since IgE from dog and rat bind to the IgE receptor of another unrelated species such as human receptor, we hypothesize that the conserved amino acids between rat and dog must contain the information specifying the receptor-binding conformational determinants. Since these conserved sequences are flanked within their respective IgE molecule with sequences that vary between dog and rat IgE, we further hypothesize that the variable IgE sequences could be exchanged between IgE from dog and rat without affecting the overall receptor-binding conformation of either IgE molecules. Using this reasoning, a safe and effective vaccine for dogs could be developed by using peptides of the present invention SEQ ID NOS: 1 to 6. The nucleotide sequences encoding antigenic peptides of the present invention were prepared using the following procedures:

Cloning of Dog CH3 Domain (SEQ ID NO: 15).

The polyneucleotide sequence encoding dog CH3 domain was assembled by a polymerase chain reaction (PCR)-based gene synthesis procedure. A set of oligonucleotide primers (listed in Table 1) was synthesized at Life Technologies Inc.

TABLE 1

Primers for cloning of Dog CH3 domain DNA (SEQ ID NO:15)

| Primer sequence | Primer name |
| --- | --- |
| AAGCGTGCCCCCCCGGAAGTCTATGCGTTTGCGAC | P173-S712 |
| TCGGGGGTCGGACTCTGAACACTTCTTGGTGCTGTC | P173-A402 |
| GACAGCACCAAGAAGTGTTCAGAGTCCGACCCCCGAGGCGTGAC | P173-S1 |
| GAGCTACCTGAGCCCACCCAGCCCCCTTGACCTGTATGTC | P173-S2 |
| CACAAGGCGCCCAAGATCACCTGCCTGGTAGTGGACCTGG | P173-S3 |
| CCACCATGGAAGGCATGAACCTGACCTGGTACCGGGAGAG | P173-S4 |
| CAAAGAACCCGTGAACCCGGGCCCTTTGAACAAGAAGGAT | P173-S5 |
| CACTTCAATGGGACGATCACAGTCACGTCTACCCTGCCAG | P173-S6 |
| TGAACACCAATGACTGGATCGAGGGCGAGACCTACTATTG | P173-S7 |
| CAGGGTGACCCACCCGCACCTGCCCAAGGACATCGTGCGC | P173-S8 |
| TCCATTGCCAAGGCCCCTGGCAAGCGTGCCCCCCCGGAAG | P173-S9 |
| CGGCGTCGCAAACGCATAGACTTCCGGGGGGGCACGCTTG | P173-A1 |
| CCAGGGGCCTTGGCAATGGAGCGCACGATGTCCTTGGGCA | P173-A2 |
| GGTGCGGGTGGGTCACCCTGCAATAGTAGGTCTCGCCCTC | P173-A3 |
| GATCCAGTCATTGGTGTTCACTGGCAGGGTAGACGTGACT | P173-A4 |
| GTGATCGTCCCATTGAAGTGATCCTTCTTGTTCAAAGGGC | P173-A5 |
| CCGGGTTCACGGGTTCTTTGCTCTCCCGGTACCAGGTCAG | P173-A6 |
| GTTCATGCCTTCCATGGTGGCCAGGTCCACTACCAGGCAG | P173-A7 |
| GTGATCTTGGGCGCCTTGTGGACATACAGGTCAAGGGGGC | P173-A8 |
| TGGGTGGGCTCAGGTAGCTCGTCACGCCTCGGGGGTCGGA | P173-A9 |

These primers were used to assemble the dog CH3 domain in a two-step PCR reaction as follows: 1) 25 cycles using an equimolar mixture of 18 primers (P173-S1 to -S9 and P173-A1 to -A9) followed by 2) dilution of the product from step 1 (0.625 ul into a 50 ul reaction) into a new reaction and carrying out 15 cycles of PCR using the two terminal primers (P173-S1 and P173-A1). All reactions used BMB Expand HF polymerase mixture and conditions specified by the manufacturer. This PCR reaction resulted in amplification of a gene sequence of the correct size.

Cloning of Nucleotide Sequence Encoding Partial Human CH3/Partial Dog CH3 Domain Fusion Protein (SEQ ID NO: 16).

This DNA sequence encodes a protein which consists of the first 63 amino acids of human CH3 domain fused to the last 53 amino acid of the dog CH3 domain. The polyneucleotide sequence encoding this construct was assembled as follows: A set of oligonucleotide primers (listed in table 2) was synthesized at Life Technologies Inc.

TABLE 2

Primers for cloning of human/dog
CH3 domain fusion DNA (SEQ ID NO:16)

| Primer sequence | Primer name |
|---|---|
| CCTCTCGGGTTGGAATCTGCACACTTCTTGGTGCTGTC | P174-A404 |
| AAGCGTGCCCCCCCGGAAGTCTATGCGTTTGCGAC | P174-S721 |
| GACAGCACCAAGAAGTGTGCAGATTCCAACCCGAGAGGGGT GAG | P174-S1 |
| CGCCTACCTAAGCCGGCCCAGCCCGTTCGACCTGTTCATC | P174-S2 |
| CGCAAGTCGCCCACGATCACCTGTCTGGTGGTGGACCTGG | P174-S3 |
| CACCCAGCAAGGGGACCGTGAACCTGACCTGGTCCCGGGC | P174-S4 |
| CAGTGGGAAGCCTGTGAACCACTCCACCAGAAAGGAGGAG | P174-S5 |
| AAGAAGGATCACTTCAATGGGACGATCACAGTCACGTCTA | P174-S6 |
| CCCTGCCAGTGAACACCAATGACTGGATCGAGGGCGAGAC | P174-S7 |
| CTACTATTGCAGGGTGACCCACCCGCACCTGCCCAAGGAC | P174-S8 |
| ATCGTGCGCTCCATTGCCAAGGCCCTGGCAAGCGTGCCC | P174-S9 |
| AAACGCATAGACTTCCGGGGGGGCACGCTTGCCAGGGGCC | P174-A1 |
| TTGGCAATGGAGCGCACGATGTCCTTGGGCAGGTGCGGGT | P174-A2 |
| GGGTCACCCTGCAATAGTAGGTCTCGCCCTCGATCCAGTC | P174-A3 |
| ATTGGTGTTCACTGGCAGGGTAGACGTGACTGTGATCGTG | P174-A4 |
| CCATTGAAGTGATCCTTCTTCCTCCTTTCTGGTGGAGT | P174-A5 |
| GGTTCACAGGCTTCCCACTGGCCCGGGACCAGGTCAGGTT | P174-A6 |
| CACGGTCCCCTTGCTGGGTGCCAGGTCCACCACCAGACAG | P174-A7 |
| GTGATCGTGGGCGACTTGCGGATGAACAGGTCGAACGGGC | P174-A8 |
| TGGGCCGGCTTAGGTAGGCGCTCACCCCTCTCGGGTTGGA | P174-A9 |

These primers were used to assemble the human CH3/dog CH3 domain fusion in a two-step PCR reaction as follows: 1) 25 cycles using an equimolar mixture of 18 primers (P174-S1 to -S9 and P174-A1 to -A9) followed by 2) dilution of the product from step 1 (0.625 μl into a 50 μl reaction) into a new reaction and carrying out 15 cycles of PCR using the two terminal primers (P174-S1 and P174-A1). All reactions used BMB Expand HF polymerase mixture and conditions specified by the manufacturer. This PCR reaction resulted in amplification of a gene sequence of the correct size (384 nucleotides).

Cloning of Chimeric Human/Dog CH3 domain (SEQ ID NO: 17).

This DNA sequence encodes a protein, which consists of alternating human/dog CH3 domain sequences. The polyneucleotide sequence encoding human CH3/conserved dog CH3 domain was assembled as follows: A set of oligonucleotide primers (listed in Table 3) was synthesized at Life Technologies Inc.

TABLE 3

Primers for cloning of human/dog
CH3 domain chimeric DNA (SEQ ID NO:17)

| Primer sequence | Primer name |
|---|---|
| GACAGCACCAAGAAGTGTGCAGATTCCAACCCGAGAGGGGT GAC | P175-S1 |
| CAGCTACCTAAGCCCGCCCAGCCCGCTGGACCTGTACATC | P175-S2 |
| CGCAAGTCGCCCAAGATCACCTGTCTGGTGGTGGACCTGG | P175-S3 |
| CACCCAGCAAGGGGACCGTGAACCTGACCTGGTCCCGGGC | P175-S4 |
| CAGTGGGAAGCCTGTGAACCACTCCACCAGAAAGGAGGAG | P175-S5 |
| AAGCAACGGAATGGGACGATCACAGTCACGTCTACCCTGC | P175-S6 |
| CAGTGGGCACCAGAGACTGGATCGAGGGCGAGACCTACTA | P175-S7 |
| TTGCAGGGTGACCCACCCGCACCTGCCCAAGGACATCGTG | P175-S8 |
| CGCTCCATTGCCAAGGCCCCTGGCAAGCGTGCCCCCCCGG | P175-S9 |
| CGTCGCAAACGCATAGACTTCCGGGGGGGCACGCTTGCCA | P175-A1 |
| GGGGCCTTGGCAATGGAGCGCACGATGTCCTTGGGCAGGT | P175-A2 |
| GCGGGTGGGTCACCCTGCAATAGTAGGTCTCGCCCTCGAT | P175-A3 |
| CCAGTCTCTGGTGCCCACTGGCAGGGTAGACGTGACTGTG | P175-A4 |
| ATCGTCCCATTCCGTTGCTTCTCCTCCTTTCTGGTGGAGT | P175-A5 |
| GGTTCACAGGCTTCCCACTGGCCCGGGACCAGGTCAGGTT | P175-A6 |
| CACGGTCCCCTTGCTGGGTGCCAGGTCCACCACCAGACAG | P175-A7 |
| GTGATCTTGGGCGACTTGCGGATGTACAGGTCCAGCGGGC | P175-A8 |
| TGGGCGGGCTTAGGTAGCTGGTCACCCCTCTCGGGTTGGA | P175-A9 |
| CCTCTCGGGTTGGAATCTGCACACTTCTTGGTGCTGTCCT | P175-A404 |
| AAGCGTGCCCCCCCGGAAGTCTATGCGTTTG | P175-S715 |

These primers were used to assemble the human CH3/dog CH3 chimeric domain in a two-step PCR reaction as follows: 1) 25 cycles using an equimolar mixture of 18 primers (P175-S1 to -S9 and P175-A1 to -A9) followed by 2) dilution of the product from step 1 (0.625 ul into a 50 ul reaction) into a new reaction and carrying out 15 cycles of PCR using the two terminal primers (P175-S1 and P175-A1). All reactions used BMB Expand HF polymerase mixture and conditions specified by the manufacturer. This PCR reaction resulted in amplification of a gene sequence of the correct size (384 nucleotides).

Cloning of HumanCH3 Domain (SEQ ID NO: 18).

The polyneucleotide sequence encoding human CH3 domain was assembled as follows: A set of oligonucleotide primers (listed in Table 4) was synthesized at Life Technologies Inc.

TABLE 4

Primers for Human CH3 domain DNA (SEQ ID NO:18)

| Primer sequence | Primer name |
|---|---|
| GACAGCACCAAGAAGTGTGCAGATTCCAACCCGAGAGGGTGAG | P176-S1 |
| CGCCTACCTAAGCCGGCCCAGCCCGTTCGACCTGTTCATC | P176-S2 |
| CGCAAGTCGCCCACGATCACCTGTCTGGTGGTGGACCTGG | P176-S3 |
| CACCCAGCAAGGGGACCGTGAACCTGACCTGGTCCCGGGC | P176-S4 |
| CAGTGGGAAGCCTGTGAACCACTCCACCAGAAAGGAGGAG | P176-S5 |
| AAGCAGCGCAATGGCACGTTAACCGTCACGTCCACCCTGC | P176-S6 |
| CGGTGGGCACCCGAGACTGGATCGAGGGGGAGACCTACCA | P176-S7 |
| GTGCAGGGTGACCCACCCCCACCTGCCCAGGGCCCTCATG | P176-S8 |
| CGGTCCACGACCAAGACCAGCGGCCCGCGTGCTGCCCCGG | P176-S9 |
| CGTCGCAAACGCATAGACTTCCGGGGCAGCACGCGGGCCG | P176-A1 |
| CTGGTCTTGGTCGTGGACCGCATGAGGGCCCTGGGCAGGT | P176-A2 |
| GGGGGTGGGTCACCCTGCACTGGTAGGTCTCCCCCTCGAT | P176-A3 |
| CCAGTCTCGGGTGCCCACCGGCAGGGTGGACGTGACGGTT | P176-A4 |
| AACGTGCCATTGCGCTGCTTCTCCTCCTTTCTGGTGGAGT | P176-A5 |
| GGTTCACAGGCTTCCCACTGGCCCGGGACCAGGTCAGGTT | P176-A6 |
| CACGGTCCCCTTGCTGGGTGCCAGGTCCACCACCAGACAG | P176-A7 |
| GTGATCGTGGGCGACTTGCGGATGAACAGGTCGAACGGGC | P176-A8 |
| TGGGCCGGCTTAGGTAGGCGCTCACCCCTCTCGGGTTGGA | P176-A9 |
| CCTCTGGGGTTGGAATCTGCACACTTCTTGGTGCT | P176-A404 |
| GCGGCCCGCGTGCTGCCCCGGAAGTCTATGCGTTTGCGAC | P176-S710 |

These primers were used to assemble the human CH3 domain in a two-step PCR reaction as follows: 1) 25 cycles using an equimolar mixture of 18 primers (P176-S1 to -S9 and P176-A1 to -A9) followed by 2) dilution of the product from step 1 (0.625 ul into a 50 ul reaction) into a new reaction and carrying out 15 cycles of PCR using the two terminal primers (P176-S1 and P176-A1). All reactions used BMB Expand HF polymerase mixture and conditions specified by the manufacturer. This PCR reaction resulted in amplification of a gene sequence of the correct size (384 nucleotides).

Cloning of Rat CH3 Domain (SEQ ID NO: 19).

The polyneucleotide sequence encoding rat CH3 domain was assembled as follows: A set of oligonucleotide primers (listed in Table 5) was synthesized at Life Technologies Inc.

TABLE 5

Primers for Rat CH3 DNA (SEQ ID NO:19)

| Primer sequence | Primer name |
|---|---|
| GACAGCACCAAGAAGTGCTCAGATGATGAGCCCCGGGTGTGAT | P177-S1 |
| TACCTACCTGATCCCACCCAGTCCCCTCGACCTGTATGAA | P177-S2 |
| AATGGGACTCCCAAACTTACCTGTCTGGTTTTGGACCTGG | P177-S3 |
| AAAGTGAGGAGAATATCACCGTGACGTGGGTCCGAGAGCG | P177-S4 |
| TAAGAAGTCTATAGGTTCGGCATCCCAGAGGAGTACCAAG | P177-S5 |
| CACCATAATGCCACAACCAGTATCACCTCCATCTTGCCAG, | P177-S6 |
| TGGATGCCAAGGACTGGATCGAAGGTGAAGGCTACCAGTG | P177-S7 |
| CAGAGTGGACCACCCTCACTTTCCCAAGCCCATTGTGCGT | P177-S8 |
| TCCATCACCAAGGCCCCAGGCAAGCGCTCAGCCCCAGAAG | P177-S9 |
| CGGCGTCGCAAACGCATAGACTTCTGGGGCTGAGCGCTTG | P177-A1 |
| CCTGGGGCCTTGGTGATGGAACGCACAATGGGCTTGGGAA | P177-A2 |
| AGTGAGGGTGGTCCACTCTGCACTGGTAGCCTTCACCTTC | P177-A3 |
| GATCCAGTCCTTGGCATCCACTGGCAAGATGGAGGTGATA | P177-A4 |
| CTGGTTGTGGCATTATGGTGCTTGGTACTCCTCTGGGATG | P177-A5 |
| CCGAACCTATAGACTTCTTACGCTCTCGGACCCACGTCAC | P177-A6 |
| GGTGATATTCTCCTCACTTTCCAGGTCCAAAACCAGACAG | P177-A7 |
| GTAAGTTTGGGAGTCCCATTTTCATACAGGTCGAGGGGAC | P177-A8 |
| TGGGTGGGATCAGGTAGGTAATCACACCCCGGGGCTCATC | P177-A9 |
| CGGGGCTCATCATCTGAGCACTTCTTGGTGCTGTCCT | P177-A401 |
| CAAGCGCTCAGCCCCAGAAGTCTATGCGTTTGCGAC | P177-S711 |

These primers were used to assemble the rat CH3 domain in a two-step PCR reaction as follows: 1) 25 cycles using an equimolar mixture of 18 primers (P177-S1 to -S9 and P177-A1 to -A9) followed by 2) dilution of the product from step 1 (0.625 µl into a 50 µl reaction) into a new reaction and carrying out 15 cycles of PCR using the two terminal primers (P177-S1 and P177-A1). All reactions used BMB Expand HF polymerase mixture and conditions specified by the manufacturer. This PCR reaction resulted in amplification of a gene sequence of the correct size (384nucleotides).

Cloning of Human CH3 for Expression in Baculovirus (SEQ ID NO: 20).

The polyneucleotide sequence encoding the IgE CH3 domain and the signal sequence from honey-bee mellitin was assembled as follows: A set of oligonucleotide primers (listed in Table 6) was synthesized at Life Technologies Inc.

TABLE 6

Primers for baculovirus expressed Human IgE CH3 domain (SEQ ID NO:20)

| Primer sequence | Primer name |
|---|---|
| GCGGATCCATGAAATTCTTAGTCAACGTTGCCCTTGTTTTAT | P158-S1 |
| GGTCGTATACATTTCTTACATCTATGCGGACAGCAACCCG | P158-S2 |
| AGAGGGGTGAGCGCCTACCTAAGCCGGCCCAGCCCGTTCG | P158-S3 |
| ACCTGTTCATCCGCAAGTCGCCCACGATCACCTGTCTGGT | P158-S4 |

TABLE 6-continued

Primers for baculovirus expressed Human IgE CH3 domain (SEQ ID NO:20)

| Primer sequence | Primer name |
|---|---|
| GGTGGACCTGGCACCCAGCAAGGGGACCGTGAACCTGACC | P158-S5 |
| TGGTCCCGGGCCAGTGGGAAGCCTGTGAACCACTCCACCA | P158-S6 |
| GAAAGGAGGAGAAGCAGCGCAATGGCACGTTAACCGTCAC | P158-S7 |
| GTCCACCCTGCCGGTGGGCACCCGAGACTGGATCGAGGGG | P158-S8 |
| GAGACCTACCAGTGCAGGGTGACCCACCCCCACCTGCCCA | P158-S9 |
| GGGCCCTCATGCGGTCCACGACCAAGACCTCCTGATGAATTC | P158-S10 |
| CGG | P158-A1 |
| CCGGAATTCATCAGGAGGTCTTTGGT | P158-A2 |
| CGTGGACCGCATGAGGGCCCTGGGCAGGTGGGGTGGGTC | P158-A3 |
| ACCCTGCACTGGTAGGTCTCCCCCTCGATCCAGTCTCGGG | P158-A4 |
| TGCCCACCGGCAGGGTGGACGTGACGGTTAACGTGCCATT | P158-A5 |
| GCGCTGCTTCTCCTCCTTTCTGGTGGAGTGGTTCACAGGC | P158-A6 |
| TTCCCACTGGCCCGGGACCAGGTCAGGTTCACGGTCCCCT | P158-A7 |
| TGCTGGGTGCCAGGTCCACCACCAGACAGGTGATCGTGGG | P158-A8 |
| CGACTTGCGGATGAACAGGTCGAACGGGCTGGGCCGGCTT | P158-A9 |
| AGGTAGGCGCTCACCCCTCTCGGGTTGCTGTCCGCATAGATGTAAGAAATGTATACGACCATAAAAACAAGGGCAACGTT | P158-S10 |

These primers were used to assemble the human CH3 domain in a two-step PCR reaction as follows: 1) 25 cycles using an equimolar mixture of 20 primers (P158-S1 to -S10 and P158-A1 to -A10) followed by 2) dilution of the product from step 1 (1.25 ul into a 50 ul reaction) into a new reaction and carrying out 10 cycles of PCR using primers (P158-S1 and P158 A1). All reactions used BMB Expand HF polymerase mixture and conditions specified by the manufacturer. This PCR reaction resulted in amplification of a gene sequence of the correct size (400 nucleotides). The PCR amplified 409 bp fragment was digested with EcoRI and BamHI enzymes and ligated to pFastBac1 plasmids digested with EcoRI and BamHI enzymes. The ligation mixture was transformed into DH5 E. coli and colonies containing the plasmid plus 409 bp insert were isolated. Plasmid DNA was prepared from DH5 cells using Quiagen columns according to the manufacturer's recommendation. The "donor plasmid" (pFastBac1-CH3) DNA was transformed into DH10Bac competent cells for transposition into the bacmid according to the Bac-To-Bac Baculovirus Expression System protocol (Life Technologies). White colonies that contained the recombinant bacmid were isolated and grown up for isolation of bacmid DNA. To isolate bacmid DNA, Concert High Purity Plasmid Isolation System (Life Technologies) was used according to the methods provided by the manufacturer. PCR analysis of recombinant bacmid was used to confirm that the CH3 gene had transposed into the bacmid. PUC/M13 amplification primers (Life Technologies) were used in reaction conditions specified by the Bac-To-Bac Expression Systems manual. The reaction yielded a single specific product 2709 base pairs in size indicating that the CH3 domain gene was inserted into the bacmid (bacmid transposed with pFastBac1 2300 bp+CH3 domain 409 bp=2709 bp).

2. Selection of Protein Carrier and Cloning of Corresponding Polyneucleotide Sequences.

The antigenic peptides of the present invention were incorporated within a carrier protein whose function is to increase the immunogenicity of the peptides and at the same time preserve the conformational attributes of these peptides that are necessary to induce the appropriate anti-IgE antibodies. For this purpose, a carrier system was developed based on the utilization of a modified CH2 and CH4 domains of human IgE. The modification of human CH2 and CH4 domain were introduced so as to avoid immunological cross-reactivity between human CH2–CH4 protein sequence and dog CH2–CH4 protein sequence. The amino acid sequence of the carrier protein SEQ ID NO: :7–9 was cloned using the following procedures:

Cloning of Human CH2 Domain (SEQ ID NO: 21):

The polynucleotide sequence encoding signal sequence::human CH2 domain was assembled by a two step polymerase chain reaction (PCR)-based gene synthesis procedures follows: A set of oligonucleotide primers (listed in Table 7) was synthesized at Life Technologies Inc.

TABLE 7

Primers for Human CH2 domain DNA (SEQ ID NO:21)

| Primer sequence | Primer name |
|---|---|
| GACTGCTAGCCATGAGTGTGCCCA | P171-S1b |
| GACTGCTAGCCATGAGTGTGCCCACTCAGGTCCTGGGGTT | P171-S1 |
| GCTGCTGCTGTGGCTTACAGATGCCAGATGTGACATCGTC | P171-S2 |
| GCCTCCAGGGACTTCACCCCGCCCTCCGTGAAGATCTTAC | P171-S3 |
| AGTCGTCCTGCGACGGCGGCGGGCACTTCCCCCCGACCAT | P171-S4 |
| CCAGCTCTACTGCCTCGTCTCTGGGTACACCCCAGGGACT | P171-S5 |
| ATCCAGATCACCTGGCTGGAGGACGGGCAGGTCATGGACG | P171-S6 |
| TGGACTTGTCCACCGCCTCTACCACGCAGGAGGGTGAGCT | P171-S7 |
| GGCCTCCACACAAAGCGAGCTCACCCTCAGCCAGAAGCAC | P171-S8 |
| TGGCTGTCAGACCGCACCTTCACCTGCCAGGTCACCTATC | P171-S9 |
| AAGGTCACACCTTTGAGGACAGCACCAAGAAGTGTCTCGA | P171-S10 |
| GACTCTCGAGACACTTCTTGGTGCT | P171-A1 |
| GTCCTCAAAGGTGTGACCTTGATAGGTGACCTGGCAGGTG | P171-A2 |
| AAGGTGCGGTCTGACAGCCAGTGCTTCTGGCTGAGGGTGA | P171-A3 |
| GCTCGCTTTGTGTGGAGGCCAGCTCACCCTCCTGCGTGGT | P171-A4 |
| AGAGGCGGTGGACAAGTCCACGTCCATGACCTGCCCGTCC | P171-A5 |
| TCCAGCCAGGTGATCTGGATAGTCCCTGGGGTGTACCCAG | P171-A6 |
| AGACGAGGCAGTAGAGCTGGATGGTCGGGGGGAAGTGCCC | P171-A7 |
| GCCGCCGTCGCAGGACGACTGTAAGATCTTCACGGAGGGC | P171-A8 |
| GGGGTGAAGTCCCTGGAGGCGACGATGTCACATCTGGCAT | P171-A9 |
| CTGTAAGCCACAGCAGCAGCAACCCCAGGACCTGAGTGGG | P171-A10 |
| TGGCTGTCAGACCGCACCTTCA | P171-S321 |
| ACTTCTTGGTGCTGTCCTCA | P171-A393 |

These primers were used to assemble the signal sequence::human CH2 domain in a two-step PCR reaction as follows: 1) 25 cycles using an equimolar mixture of 20 primers (P171-S1 to -S10 and P171-A1 to -A10) followed by 2) dilution of the product from step 1 (0.625 ul into a 50 ul reaction) into a new reaction and carrying out 15 cycles of PCR using the two terminal primers (P171-S1b and P171-A1). All reactions used BMB Expand HF polymerase mixture and conditions specified by the manufacturer. This PCR reaction resulted in amplification of a gene sequence of the correct size. The amplified gene was then cloned into (pGEM-T) vector at the T/A cloning site. The nucleotide sequence of the amplified fragment was determined by automated fluorescent DNA sequencing.

Cloning of Human CH4 Domain (SEQID# 22).

The polynucleotide sequence encoding human CH4 domain was assembled by a two step polymerase chain reaction (PCR)-based gene synthesis procedure as follows: A set of oligonucleotide primers (listed in Table 8) was synthesized at Life Technologies Inc.

TABLE 8

Primers for Human CH4 DNA (SEQ ID NO:22)

| Primer sequence | Primer name |
|---|---|
| GACTCTCGAGGAAGTCTATGCGTT | P172-S1b |
| GACTCTCGAGGAAGTCTATGCGTTTGCGACGCCGGAGTGG | P172-S1 |
| CCGGGGAGCCGGGACAAGCGCACCCTCGCCTGCCTGGTGC | P172-S2 |
| AGAACTTCATGCCTGAGGACATCTCGCTGCGCTGGGTGCA | P172-S3 |
| CAACGAGGTGCAGCTCCCGGACGCCCGGCACAGCACGACG | P172-S4 |
| CAGCCCCGCAAGACCAAGGGCTCCGGCTTCTTCGTCTTCA | P172-S5 |
| GCCGCCTGGCGGTGACCAGGGCCGAATGGCAGGAGAAAGA | P172-S6 |
| TGAGTTCATCTGCCGTGCAGTCCATGAGGCAGCGAGCCCC | P172-S7 |
| TCACAGACCGTCCAGCGAGCGGTGTCTGTAAATCCCGGTA | P172-S8 |
| GACTGAATTCTCATTTACCGGGATT | P172-A1b |
| GACTGAATTCTCATTTACCGGGATTTACAGACACC | P172-A1 |
| GCTCGCTGGACGGTCTGTGAGGGGCTCGCTGCCTCATGGA | P172-A2 |
| CTGCACGGCAGATGAACTCATCTTTCTCCTGCCATTCGGC | P172-A3 |
| CCTGGTCACCGCCAGGCGGCTGAAGACGAAGAAGCCGGAG | P172-A4 |
| CCCTTGGTCTTGCGGGGCTGCGTCGTGCTGTGCCGGGCGT | P172-A5 |
| CCGGGAGCTGCACCTCGTTGTGCAGCCAGCGCACCGAGAT | P172-A6 |
| GTCCTCAGGCATGAAGTTCTGCACCAGGCAGGCGAGGGTG | P172-A7 |
| CGCTTGTCCCGGCTCCCCGGCCACTCCGGCGTCGCAAACG | P172-A8 |
| GAAGTCTATGCGTTTGCGACG | P172-S11 |
| GCAGCCAGCGCACCGAGATGTC | P172-A119 |

These primers were used to assemble the human CH4 domain in a two-step PCR reaction as follows: 1) 25 cycles using an equimolar mixture of 16 primers (P172-S1 to -S8 and P172-A1 to -A8) followed by 2) dilution of the product from step 1 (0.625 ul into a 50 ul reaction) into a new reaction and carrying out 15 cycles of PCR using the two terminal primers (P172-S1b and P172-A1b). All reactions used BMB Expand HF polymerase mixture and conditions specified by the manufacturer. This PCR reaction resulted in amplification of a gene sequence of the correct size. The amplified gene was then cloned into (pGEM-T) vector at the T/A cloning site. The nucleotide sequence of the amplified fragment was determined by automated fluorescent DNA sequencing.

3. Cloning of Genes Encoding Fusion Protein Vaccines:

Polynucleotide sequences encoding fusion proteins for use as vaccines (SEQ ID NO: 24–28) of the present invention were prepared as follows.

Cloning of IgE-1 Vaccine Construct (SEQ ID NO: 24):

The insert in construct IgE-1 consists of the signal sequence-human CH2 domain followed by the dog CH3 domain followed by the human CH4 domain. Assembly of the insert for IgE-1 consisted of using the signal sequence-human CH2 domain as a template for one PCR reaction, and the human CH4 domain as a template for a second PCR reaction. In these two reactions, terminal primers were used to generate regions of homology with the dog CH3 domain, so that the two ends of the dog CH3 domain DNA fragment would hybridize to the two human domain DNA fragments and the three fragments would serve as "megaprimers" in a PCR reaction. The dog CH3 domain was engineered to contain overlapping sequence on either end to the two human domain fragments (CH2 homology on the 5' end and CH4 homology on the 3' end). Then, the three PCR fragments (human CH2, dog CH3 and human CH4) were mixed in a final PCR reaction utilizing the terminal primers to generate a full-length product. The procedure is outlined as follows: Fragment 1: (signal sequence-human CH2 domain) 413 bp fragment resulting from amplification of human CH2 domain with primers P171-S1b and P173-A402; fragment was amplified in 35 cycles of PCR, followed by gel purification. All reactions used BMB Expand HF polymerase mixture and conditions specified by the manufacturer. Fragment 2: (dog CH3 domain) 384 bp fragment described above; gel purified Fragment 3: (human CH4 domain) 340 bp fragment resulting from amplification of human CH4 domain with primers P173-S712 and P172-A1b; fragment was amplified in 35 cycles of PCR, followed by gel purification. All reactions used BMB Expand HF polymerase mixture and conditions specified by the manufacturer. The three fragments were added in approximately equimolar amounts to a final PCR reaction using the two terminal primers P171-S1b and P172-A1b, and carrying out 35 cycles of PCR. All reactions used BMB Expand HF polymerase mixture and conditions specified by the manufacturer. This PCR reaction resulted in amplification of a gene sequence of the correct size (1.1 kb). The resulting fragment was digested with EcoR I and NheI and subcloned into the corresponding sites of the plasmid pCI-neo. The nucleotide sequence of the amplified fragment was determined by automated fluorescent DNA sequencing.

Cloning of Construct IgE-2 (SEQ ID NO: 25).

The insert in construct IgE-2 consists of the signal sequence-human CH2 domain followed by the human CH3/dog domain, followed by the human CH4 domain. Assembly of the insert for IgE-2 consisted of using the signal sequence-human CH2 domain as a template for one PCR reaction, and the human CH4 domain as a template for a second PCR reaction. In these two reactions, terminal primers were used to generate regions of homology with the human CH3/dog CH3 domain, so that the two ends of the human CH31dog CH3 domain DNA fragment would hybridize to the two human domain DNA fragments and the three fragments would serve as "megaprimers" in a PCR reaction. The human CH3/dog CH3 domain was engineered to contain overlapping sequence on either end to the two human domain fragments (CH2 homology on the 5' end and CH4 homology on the 3' end). Then, the three PCR fragments (human CH2, human CH3/dog CH3, human CH4) were mixed in a final PCR reaction utilizing two terminal primers to generate a full length product. The procedure is outlined as follows: Fragment 1: (signal sequence-human CH2 domain) 414 bp fragment resulting from amplification of human CH2 domain with primers P171-S1b and P174-A404; fragment was amplified in 25 cycles of PCR, followed by gel purification. All reactions used BMB Expand HF polymerase mixture and conditions specified by the manufacturer. Fragment 2: (human CH3/dog CH3 domain) 384 bp fragment described above; gel purified Fragment 3: (human CH4 domain) 340 bp fragment resulting from amplification of human CH4 domain with primers P174-S721 and P172-A1b; fragment was amplified in 25 cycles of PCR, followed by gel purification. All reactions used BMB Expand HF polymerase mixture and conditions specified by the manufacturer. The three gel-purified fragments were added in approximately equimolar amounts to a final PCR reaction using the two terminal primers P171-S1b and P172-A1b, and carrying out 35 cycles of PCR. All reactions used BMB Expand HF polymerase mixture and conditions specified by the manufacturer. This PCR reaction resulted in amplification of a gene sequence of the correct size (1.1 kb). The resulting fragment was digested with EcoR I and Nhe I and subcloned into the corresponding sites of the plasmid pCI-neo. The nucleotide sequence of the amplified fragment was determined by automated fluorescent DNA sequencing.

Cloning of IgE-3 Vaccine Construct (SEQ ID NO: 26).

The insert in construct IgE-3 consists of the signal sequence-human CH2 domain followed by the human CH3/conserved dog CH3 sequence, followed by the human CH4 domain. Assembly of the insert for IgE-3 consisted of using the signal sequence-human CH2 domain as a template for one PCR reaction, and the human CH4 domain as a template for a second PCR reaction. In these two reactions, terminal primers were used to generate regions of homology with the human CH3/conserved dog CH3 sequence, so that the two ends of the middle (human CH3/conserved dog CH3 domain) DNA fragment would hybridize to the two human domain DNA fragments and the three fragments would serve as "megaprimers" in a PCR reaction. The human CH3/conserved dog CH3 sequence was engineered to contain overlapping sequence on either end to the two human domain fragments (CH2 homology on the 5' end and CH4 homology on the 3' end). Then, the three PCR fragments (human CH2, human CH3/conserved dog CH3, human CH4) were mixed in a final PCR reaction utilizing two terminal primers to generate a full length product. The procedure is outlined as follows: Fragment 1: (signal sequence-human CH2 domain) 414 bp fragment resulting from amplification of human CH2 domain with primers P171-S1b and P175-A404; fragment was amplified in 25 cycles of PCR, followed by gel purification. All reactions used BMB Expand HF polymerase mixture and conditions specified by the manufacturer. Fragment 2: (human CH3/conserved dog CH3 sequence) 384 bp fragment described above; gel purified Fragment 3: (human CH4 domain) 340 bp fragment resulting from amplification of human CH4 domain with primers P175-S715 and P172-A1b; fragment was amplified in 25 cycles of PCR, followed by gel purification. All reactions used BMB Expand HF polymerase mixture and conditions specified by the manufacturer. The three gel-purified fragments were added in approximately equimolar amounts to a final PCR reaction using the two terminal primers P171-S1b and P172-A1b, and carrying out 35 cycles of PCR. All reactions used BMB Expand HF polymerase mixture and conditions specified by the manufacturer. This PCR reaction resulted in amplification of a gene sequence of the correct size (1.1 kb). The resulting fragment was digested with EcoR I and Nhe I and subcloned into the corresponding sites of the plasmid pCI-neo. The nucleotide sequence of the amplified fragment was determined by automated fluorescent DNA sequencing.

Cloning of IgE-4 Vaccine Construct (SEQ ID NO: 27).

The insert in construct IgE-4 consists of the signal sequence-human CH2 domain followed by the human CH3 domain followed by the human CH4 domain. Assembly of the insert for IgE-4 consisted of using the signal sequence-human CH2 domain as a template for one PCR reaction, and the human CH4 domain as a template for a second PCR reaction. In these two reactions, terminal primers were used to generate regions of homology with the human CH3 domain, so that the two ends of the middle (human CH3 domain) DNA fragment would hybridize to the two terminal human domain DNA fragments and the three fragments would serve as "megaprimers" in a PCR reaction. The human CH3 domain sequence was engineered to contain overlapping sequence on either end to the two human domain fragments (CH2 homology on the 5' end and CH4 homology on the 3' end). Then, the three PCR fragments (human CH2, human CH3, human CH4) were mixed in a final PCR reaction utilizing two terminal primers to generate a full length product. The procedure is outlined as follows: Fragment 1: (signal sequence-human CH2 domain) 414 bp fragment resulting from amplification of human CH2 domain with primers P171-S1b and P176-A404; fragment was amplified in 25 cycles of PCR, followed by gel purification. All reactions used BMB Expand HF polymerase mixture and conditions specified by the manufacturer. Fragment 2: (human CH3 domain) 384 bp fragment described above; gel purified Fragment 3: (human CH4 domain) 345 bp fragment resulting from amplification of human CH4 domain with primers P176-S710 and P172-A1b; fragment was amplified in 25 cycles of PCR, followed by gel purification. All reactions used BMB Expand HF polymerase mixture and conditions specified by the manufacturer. The three gel-purified fragments were added in approximately equimolar amounts to a final PCR reaction using the two terminal primers P171-S1b and P172-A1b, and carrying out 35 cycles of PCR. All reactions used BMB Expand HF polymerase mixture and conditions specified by the manufacturer. This PCR reaction resulted in amplification of a gene sequence of the correct size (1.1 kb). The resulting fragment was digested with EcoR I and Nhe I and subcloned into the corresponding sites of the plasmid pCI-neo. The nucleotide sequence of the amplified fragment was determined by automated fluorescent DNA sequencing.

Cloning of IgE-5 Vaccine Construct (SEQ ID NO: 28).

The insert in construct IgE-5 consists of the signal sequence-human CH2 domain followed by the rat CH3 domain followed by the human CH4 domain. Assembly of the insert for IgE-5 consisted of using the signal sequence-human CH2 domain as a template for one PCR reaction, and the human CH4 domain as a template for a second PCR reaction. In these two reactions, terminal primers were used to generate regions of homology with the rat CH3 domain, so that the two ends of the middle (rat CH3 domain) DNA fragment would hybridize to the two terminal human domain DNA fragments and the three fragments would serve as "megaprimers" in a PCR reaction. The rat CH3 domain sequence was engineered to contain overlapping sequence on either end to the two human domain fragments (CH2 homology on the 5' end and CH4 homology on the 3' end). Then, the three PCR fragments (human CH2, rat CH3, human CH4) were mixed in a final PCR reaction utilizing two terminal primers to generate a full-length product. The procedure is outlined as follows: Fragment 1: (signal sequence-human CH2 domain) 411 bp fragment resulting from amplification of human CH2 domain with primers P171-S1b and P177-A401; fragment was amplified in 25 cycles of PCR, followed by gel purification. All reactions used BMB Expand HF polymerase mixture and conditions specified by the manufacturer. Fragment 2: (rat CH3 domain) 384 bp fragment described above; gel purified Fragment 3: (human CH4 domain) 341 bp fragment resulting from amplification of human CH4 domain (IgE-6(3')) with primers P177-S711 and P172-A1b; fragment was amplified in 25 cycles of PCR, followed by gel purification. All reactions used BMB Expand HF polymerase mixture and conditions specified by the manufacturer. The three gel-purified fragments were added in approximately equimolar amounts to a final PCR reaction using the two terminal primers P171-S1b and P172-A1b, and carrying out 35 cycles of PCR. All reactions used BMB Expand HF polymerase mixture and conditions specified by the manufacturer. This PCR reaction resulted in amplification of a gene sequence of the correct size (1.1 kb). The resulting fragment was digested with EcoR I and Nhe I and subcloned into the corresponding sites of the plasmid pCI-neo. The nucleotide sequence of the amplified fragment was determined by automated fluorescent DNA sequencing.

4. Transfection, Expression and Reactivity of Vaccines with Anti-canine IgE Antibodies.
Expression of IgE CH3 Domain in Insect Cells:

Sf9 cells (Life Technologies) derived from *Spodoptera frugiperda* were transfected with the Recombinant Bacmid DNA using Cell FECTIN reagent (Life Technologies) following the Bac-To-Bac Expression System protocol. At 72 hours supernates were passaged to fresh subconfluent Sf9 cells. At 7 days post infection cytopathic effect (CPE) was evident. Supernates were harvested and stored at 4C protected from light. Samples were analyzed by electrophoresis (4–12% Bis-Tris Novex NuPage system reducing conditions). One of the duplicate gels was stained with coomassie blue and the other was transferred to PVDF membrane (Novex) using standard western blot transfer method. The membrane was probed with rabbit #145 RBS-2 polyclonal antiserum followed by AP-rec Protein G (Zymed). A distinct band of approximately 14.5 kDa was evident in both the coomassie stained gel (FIG. 1) and western blot (FIG. 2) indicating expression of the CH3 protein.

Sequences of the present invention are described in Table 9.

TABLE 9

Sequence Listings

| Composition | Sequence ID# | Protein/DNA |
|---|---|---|
| Dog CH3 domain | SEQ ID NO: 1 | Protein |
| Human/dog CH3 domain fusion | SEQ ID NO: 2 | Protein |
| Human/dog CH3 domain chimera | SEQ ID NO: 3 | protein |
| Human CH3 domain | SEQ ID NO: 4 | Protein |
| Rat CH3 domain | SEQ ID NO: 5 | Protein |
| Human CH3 domain (baculovirus expressed) | SEQ ID NO: 6 | protein |
| Modified human CH2 domain | SEQ ID NO: 7 | Protein |
| Modified human CH4 domain | SEQ ID NO: 8 | Protein |
| human CH2–CH4 carrier protein | SEQ ID NO: 9 | protein |
| IgE-1 fusion protein | SEQ ID NO: 10 | Protein |
| IgE-2 fusion protein | SEQ ID NO: 11 | Protein |
| IgE-3 fusion protein | SEQ ID NO: 12 | protein |
| IgE-4 fusion protein | SEQ ID NO: 13 | Protein |
| IgE-5 fusion protein | SEQ ID NO: 14 | protein |
| Dog CH3 domain | SEQ ID NO: 15 | DNA |
| Human/dog CH3 domain fusion | SEQ ID NO: 16 | DNA |
| Human/dog CH3 domain chimera | SEQ ID NO: 17 | DNA |
| Human CH3 domain | SEQ ID NO: 18 | DNA |
| Rat CH3 domain | SEQ ID NO: 19 | DNA |
| Human CH3 domain (baculovirus expressed) | SEQ ID NO: 20 | DNA |
| Modified human CH2 domain | SEQ ID NO: 21 | DNA |
| Modified human CH4 domain | SEQ ID NO: 22 | DNA |
| Modified human CH2–CH4 carrier protein | SEQ ID NO: 23 | DNA |
| IgE-1 construct | SEQ ID NO: 24 | DNA |
| IgE-2 construct | SEQ ID NO: 25 | DNA |
| IgE-3 construct | SEQ ID NO: 26 | DNA |
| IgE-4 construct | SEQ ID NO: 27 | DNA |
| IgE-5 construct | SEQ ID NO: 28 | DNA |

What is claimed is:

1. An isolated antigenic protein comprising an amino acid sequence of SEQ ID NO: 2 or SEQ ID NO: 3, that induces an anti-IgE immune response that does not cause anaphylaxis when administered to an animal.

2. An isolated antigenic protein comprising an amino acid sequence of SEQ ID NO: 2, SEQ ID NO: 3, SEQ ID NO: 11, SEQ ID NO: 12, SEQ ID NO: 13, or SEQ ID NO: 14, that induces an anti-IgE immune response that does not cause anaphylaxis when administered to an animal.

3. An isolated antigenic fusion protein comprising an amino acid sequence of SEQ ID NO: 10, SEQ ID NO: 11, SEQ ID NO: 12, SEQ ID NO: 13, or SEQ ID NO: 14, that induces an anti-IgE immune response that does not cause anaphylaxis when administered to an animal.

* * * * *